United States Patent
Cai et al.

(10) Patent No.: US 7,317,029 B2
(45) Date of Patent: Jan. 8, 2008

(54) 3,5-DISUBSTITUTED-[1,2,4]-OXADIAZOLES AND ANALOGS AS ACTIVATORS OF CASPASES AND INDUCERS OF APOPTOSIS AND THE USE THEREOF

(75) Inventors: Sui Xiong Cai, San Diego, CA (US); Han-Zhong Zhang, San Diego, CA (US); Jared D. Kuemmerle, Del Mar, CA (US); Hong Zhang, San Diego, CA (US); William E. Kemnitzer, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 11/593,030

(22) Filed: Nov. 6, 2006

(65) Prior Publication Data

US 2007/0112003 A1    May 17, 2007

Related U.S. Application Data

(62) Division of application No. 10/737,865, filed on Dec. 18, 2003, now Pat. No. 7,144,876.

(60) Provisional application No. 60/433,953, filed on Dec. 18, 2002.

(51) Int. Cl.
  *A61K 31/41* (2006.01)
  *C07D 271/06* (2006.01)
(52) U.S. Cl. .................................. 514/364; 548/131
(58) Field of Classification Search ............... 514/364; 548/131
  See application file for complete search history.

(56) References Cited

U.S. PATENT DOCUMENTS

| | | | |
|---|---|---|---|
| 3,772,441 A | 11/1973 | Lombardino | |
| 3,879,404 A | 4/1975 | Baldwin et al. | |
| 4,791,124 A | 12/1988 | Lutomski et al. | |
| 5,134,142 A | 7/1992 | Matsuo et al. | |
| 5,464,848 A | 11/1995 | Diana et al. | |
| 6,121,260 A | 9/2000 | Thurkauf et al. | |
| 6,277,873 B1 | 8/2001 | Yu et al. | |
| 7,144,876 B2 * | 12/2006 | Cai et al. | 514/171 |
| 2003/0045546 A1 | 3/2003 | Cai et al. | |

FOREIGN PATENT DOCUMENTS

WO    WO 96/20721 A1    11/1996
WO    WO 02/100826     12/2002

OTHER PUBLICATIONS

Rice and Nuss (Bioorganic & Medicinal Chemistry Letters, 11, 2001, pp. 753-755.).*
Batleux, F., et al., "Gene Therapy of Experimental Autoimmune Thyroiditis by In Vivo Administration of Plasmid DNA Coding for Fas Ligand," *J. Immunol.* 162:603-608, The American Association of Immunologists (1999).
Boirivant, M., et al., "Lamina Propria T Cells in Crohn's Disease and Other Gastrointestinal Inflammation Show Defective CD2 Pathway-Induced Apoptosis," *Gastroenterology* 116:557-565, The American Gastroenterological Association (1999).
Chinnaiyan, A.M., et al., "The inhibition of pro-apopotic ICE-like proteases enhances HIV replication," *Nat. Med.* 3:333-337, Nature Publishing Co. (1997).
Coven, T.R., et al., "PUVA-induced lymphocyte apoptosis: Mechanism of action in psoriasis," *Photodermatol. Photoimmunol. Photomed.* 15:22-27, Munksgaard (1999).
Ellis, R.E., et al., "Mechanisms and Functions of Cell Death," *Ann. Rev. Cell Biol.* 7:663-698, Annual Reviews, Inc. (1991).
Friesen, C., et al., "Involvement of the CD95 (APO-1/FAS) receptor/ligand system in drug-induced apoptosis in leukemia cells," *Nat. Med.* 2:574-577, Nature Publishing Co. (1996).
Greenwald, R.B., "Drug Delivery Systems Employing 1,4- or 1,6-Elimination: Poly(ethylene glycol) Prodrugs of Amine-Containing Compounds," *J. Med. Chem.* 42:3657-3667, American Chemical Society (1999).
Heenen, M., et al., "Methotrexate induces apoptotic cell death in human keratinocytes," *Arch. Dermatol. Res.* 290:240-245, Springer-Verlag (1998).
Infante, A.J., et al., "The clinical spectrum in a large kindred with autoimmune lymphoproliferate syndrome caused by a Fas mutation that impairs lymphocyte apoptosis," *J. Pediatr.* 133:629-633, Mosby, Inc. (1998).
Leu, Y.-L., et al., "Design and Synthesis of Water-Soluble Glucuronide Derivatives of Camptothecin for Cancer Prodrug Monotherapy and Antibody-Directed Enzyme Prodrug Therapy (ADEPT)," *J. Med. Chem.* 42:3623-3628, American Chemical Society (1999).
López-Hoyos, M., et al., "Regulation of B cell apoptosis by Bcl-2 and Bcl-$X_L$ and its role in the development of autoimmune diseases (Review)," *Int. J. Mol. Med.* 1:475-483, D.A. Spandidos (1998).
Los, M., et al., "Cross-Resistance of CD95- and Drug-Induced Apoptosis as a Consequence of Deficient Activation of Capases (ICE/Ced-3 Proteases)," *Blood* 90:3118-3129, W. B. Saunders Co. (1997).
O'Reilly, L.A., and Strasser, A., "Apoptosis and autoimmune disease," *Inflamm. Res.* 48:5-21, Birkhäuser Verlag (1999).

(Continued)

*Primary Examiner*—Rebecca Anderson
*Assistant Examiner*—Susannah Chung
(74) *Attorney, Agent, or Firm*—Sterne, Kessler, Goldstein & Fox P.L.L.C.

(57) ABSTRACT

Disclosed are 3,5-disubstituted-[1,2,4]-oxadiazoles and analogs thereof, represented by the Formula I:

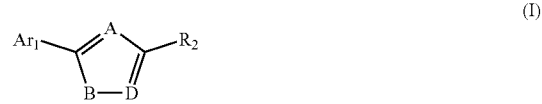

wherein $Ar_1$, $R_2$, A, B and D are defined herein. The present invention relates to the discovery that compounds having Formula I are activators of caspases and inducers of apoptosis. Therefore, the activators of caspases and inducers of apoptosis of this invention may be used to induce cell death in a variety of clinical conditions in which uncontrolled growth and spread of abnormal cells occurs.

12 Claims, No Drawings

OTHER PUBLICATIONS

Ohsako, S., and Elkon, K.B., "Apoptosis in the effector phase of autoimmune diabetes, multiple sclerosis and thyroiditis," *Cell Death Differ.* 6:13-21, Stockton Press (1999).

Orrenius, S., "Apoptosis: molecular mechanisms and implications for human disease," *J. Internal Med.* 237:529-536, Blackwell Science Ltd. (1995).

Ozawa, M., et al., "312-nanometer Ultraviolet B Light (Narrow-Band UVB) Induces Apoptosis of T Cells within Psoriatic Lesions," *J. Exp. Med.* 189:711-718, The Rockefeller University Press (1999).

Savill, J., "Apoptosis in resolution of inflammation," *J. Leukoc. Biol.* 61:375-380, The Society for Leukocyte Biology (1997).

Schmitt, E., et al., "The Bcl-xL and BAX-α control points: modulation of apoptosis induced by cancer chemotherapy and relation to TPCK-sensitive protease and caspase activation," *Biochem. Cell Biol.* 75:301-314, National Research Council of Canada (1997).

Tai, D.-I., et al., "Activation of Nuclear Factor κB in Hepatitis C Virus Infection: Implications for Pathogenesis and Hepatocarcinogenesis," *Hepatology* 3:656-664, W.B. Saunders Co. (Mar. 2000).

Thornberry, N.A., "The caspase family of cysteine proteases," *Brit. Med. Bull.* 53:478-490, Oxford University Press (1997).

Thornberry, N.A., "Caspases: key mediators of apoptosis," *Chem. Biol.* 5:R97-R103, Current Biology Ltd. (1998).

Vaishnaw, A.K., et al., "The molecular basis for apoptoic defects in patients with CD95 (Fas/Apo-1) mutations," *J. Clin. Invest.* 103:355-363, The American Society for Clinical Investigation (1999).

Wakisaka, S., et al., "Modulation by proinflammatory cytokines of Fas/Fas ligand-mediated apoptotic cell death of synovial cells in patients with rheumatoid arthritis (RA)," *Clin. Exp. Immunol.* 114:119-128, Blackwell Science (1998).

Wyllie, A.H., et al., "Cell Death: The Significance of Apoptosis," *Int. Rev. Cyt.* 68:251-306, Academic Press, Inc. (1980).

Wyllie, A.H., "Cell death: a new classification separating apoptosis from necrosis," in *Cell death in biology and pathology*, Bowen and Lockshin, eds., Chapman and Hall, London, England, pp. 9-34 (1981).

Zhou, T., et al., "Bisindolylmaleimide VIII facilitates Fas-mediated apoptosis and inhibits T cell-mediated autoimmune diseases," *Nat. Med.* 5:42-48, Nature Publishing Co. (1999).

D'Andrea, G.M., and Seidman, A.D., "Docetaxel and Paclitaxel in Breast Cancer Therapy: Present Status and Future Prospects," *Semin. Oncol.* 24:S13-27-S13-44, W.B. Saunders (1997).

Rice, K.D., and Nuss, J.M., et al., "An improved synthesis of 1,2,4-oxadiazoles on sold support," *Bioorg. & Med. Chem. Lett.* 11:753-755, Elsevier Science Ltd. (2001).

CAPlus Database, Accession No. 1993:101879, Abstract of Gao, F., and Yan, J., "Antihydatic agent: synthesis of 3-substituted phenyl-5-substituted-1,2,4-oxadiazoles," *Zhongguo Yiyao Gongye Zazhi* 23:251-254, Zygzea (1992).

CAPlus Database, Accession No. 124:343192, Abstract of Chimirri, A., et al., "Synthesis and antitumor activity evaluation of Δ2-1,2,3-oxadiazoline derivatives," *Farmaco* 51:125-129, Societa Chimica Italiana (1996).

Iino, M., et al., "Rational Design and Evaluation of New Lead Compound Structures for Selective βARK1 Inhibitors," *J. Med. Chem.* 45:2150-2159, American Chemical Society (2002).

International Search Report for PCT Patent Application No. PCT/US03/40308, mailed May 19, 2004, Alexandria, VA.

\* cited by examiner

3,5-DISUBSTITUTED-[1,2,4]-OXADIAZOLES AND ANALOGS AS ACTIVATORS OF CASPASES AND INDUCERS OF APOPTOSIS AND THE USE THEREOF

BACKGROUND OF THE INVENTION

1. Field of the Invention

This invention is in the field of medicinal chemistry. In particular, the invention relates to 3,5-disubstituted-[1,2,4]-oxadiazoles and analogs, and the discovery that these compounds are activators of caspases and inducers of apoptosis. The invention also relates to the use of these compounds as therapeutically effective anti-cancer agents.

2. Related Art

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material)(Orrenius, S., *J. Internal Medicine* 237:529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow growing tumors, e.g. colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

SUMMARY OF THE INVENTION

The present invention is related to the discovery that 3,5-disubstituted-[1,2,4]-oxadiazoles and analogs, as represented in Formula I, are activators of the caspase cascade and inducers of apoptosis. Thus, an aspect of the present invention is directed to the use of compounds of Formula I as inducers of The compounds of the present invention are represented by Formula I:

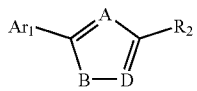

(I)

or pharmaceutically acceptable salts or prodrugs or tautomers thereof, wherein:

$Ar_1$ is optionally substituted aryl or optionally substituted heteroaryl;

$R_2$ is optionally substituted and selected from the group consisting of arylalkyl, arylalkenyl, aryloxy, arylalkyloxy, phenoxymethyl, anilino, benzylamino, benzylideneamino, benzoylamino, heterocycle, carbocycle and $Ar_2$, wherein $Ar_2$ is optionally substituted aryl or optionally substituted heteroaryl; and A, B and D independently are C, $CR_{10}$, $C(R_{10})R_{11}$, N, $NR_{12}$, O or S, wherein $R_{10}$ and $R_{11}$, are at each occurrence independently hydrogen, optionally substituted alkyl, optionally substituted cycloalkyl or optionally substituted aryl and $R_{12}$ is at each occurrence independently hydrogen, optionally substituted alkyl, optionally substituted cycloalkyl or optionally substituted aryl, provided that valency rules are not violated.

A second aspect of the present invention is to provide a method for treating, preventing or ameliorating neoplasia and cancer by administering a compound of one of the Formula I to a mammal in need of such treatment.

Many of the compounds within the scope of the present invention are novel compounds. Therefore, a third aspect of the present invention is to provide novel compounds of Formula I, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of one of the Formula I in admixture with one or more pharmaceutically acceptable carriers or diluents.

A fifth aspect of the present invention is directed to methods for the preparation of novel compounds of Formula I.

DETAILED DESCRIPTION OF THE INVENTION

The present invention arises out of the discovery that 3,5-disubstituted-[1,2,4]-oxadiazoles and analogs, as represented in Formula I, are potent and highly efficacious activators of the caspase cascade and inducers of apoptosis. Therefore, compounds of Formula I are useful for treating disorders responsive to induction of apoptosis.

Specifically, compounds of the present invention are represented by Formula I:

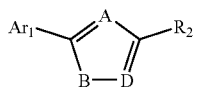

(I)

or pharmaceutically acceptable salts or prodrugs or tautomers thereof, wherein:

$Ar_1$ is optionally substituted aryl or optionally substituted heteroaryl;

$R_2$ is optionally substituted and selected from the group consisting of arylalkyl, arylalkenyl, aryloxy, arylalkyloxy, phenoxymethyl, anilino, benzylamino, benzylideneamino, benzoylamino, heterocycle, carbocycle and $Ar_2$, wherein $Ar_2$ is optionally substituted aryl or optionally substituted heteroaryl; and A, B and D independently are C, $CR_{10}$, $C(R_{10})R_{11}$, N, $NR_{12}$, O or S, wherein $R_{10}$ and $R_{11}$, are at each occurrence independently hydrogen, optionally substituted alkyl, optionally substituted cycloalkyl or optionally substituted aryl and $R_{12}$ is at each occurrence independently hydrogen, optionally substituted alkyl, optionally substituted cycloalkyl or optionally substituted aryl, provided that valency rules are not violated. Preferably, $R_{10}$, $R_{11}$ and $R_{12}$ are hydrogen, alkyl, cycloalkyl or aryl; more preferably, $R_{10}$, $R_{11}$, and $R_{12}$ are hydrogen, alkyl or cycloalkyl.

Preferred compounds of Formula I include compounds wherein A is N, B is O and D is N. Another group of preferred compounds of Formula I include compounds wherein A is N, B is $NR_{12}$ and D is N. Another group of preferred compounds of Formula I include compounds wherein A is N, B is $C(R_{10})R_{11}$ and D is N. Another group of preferred compounds of Formula I include compounds wherein A is N, B is $C(R_{10})R_{11}$ and D is $CR_{10}$. Another group of preferred compounds of Formula I include compounds wherein A is $CR_{10}$, B is $NR_{12}$ and D is N. Another group of preferred compounds of Formula I include compounds wherein A is $CR_{10}$, B is O and D is N. Another group of preferred compounds of Formula I include compounds wherein A is $CR_{10}$, B is $NR_{12}$ and D is $CR_{10}$. Another group of preferred compounds of Formula I include compounds wherein A is $CR_{10}$, B is O and D is $CR_{10}$.

Preferred compounds of Formula I include compounds wherein $Ar_1$ is phenyl, naphthyl, pyridyl, quinolyl, isoquinolyl, isoxazolyl, pyrazolyl, imidazolyl, thienyl, furyl or pyrrolyl, each of which is optionally substituted. More preferably, $Ar_1$ is isoxazolyl, pyrazolyl, imidazolyl, thienyl, furyl or pyrrolyl.

Preferred compounds of Formula I include compounds wherein $R_2$ is phenyl, naphthyl, pyridyl, quinolyl, isoquinolyl, isoxazolyl, pyrazolyl, imidazolyl, thienyl, furyl, pyrrolyl, pyrazolo[1,5-a]pyrimidinyl, morpholinyl, piperazinyl, piperidinyl, cyclohexyl, benzyl, benzyloxy, phenylvinyl, phenethyl, phenoxymethyl, benzylamino, benzoylamino, or benzylideneamino, each of which is optionally substituted. More preferably $R_2$ is phenyl, naphthyl, pyridyl, quinolyl, isoquinolyl, isoxazolyl, pyrazolyl, imidazolyl, thienyl, furyl, pyrrolyl, morpholinyl, piperazinyl, piperidinyl, or cyclohexyl. Most preferably $R_2$ is phenyl, pyridyl or morpholinyl.

One group of preferred compounds of the present invention are represented by Formula II:

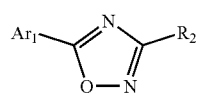

(II)

or pharmaceutically acceptable salts, prodrugs or tautomers thereof, wherein:

$Ar_1$ is optionally substituted aryl or optionally substituted heteroaryl;

$R_2$ is optionally substituted and selected from the group consisting of arylalkyl, arylalkenyl, aryloxy, arylalkyloxy, phenoxymethyl, anilino, benzylamino, benzylideneamino, benzoylamino, heterocycle, carbocycle and Ar$_2$, wherein Ar$_2$ is optionally substituted aryl or optionally substituted heteroaryl.

Preferred compounds of Formula II include compounds wherein Ar$_1$ is phenyl, naphthyl, pyridyl, quinolyl, isoquinolyl, isoxazolyl, pyrazolyl, imidazolyl, thienyl, furyl or pyrrolyl; Preferably Ar$_1$ is phenyl, pyridyl, isoxazolyl, pyrazolyl, imidazolyl, thienyl, furyl or pyrrolyl, each of which is optionally substituted; More preferably, Ar$_1$ is isoxazolyl, pyrazolyl, imidazolyl, thienyl, furyl or pyrrolyl, each of which is optionally substituted.

Preferably the compounds useful in this aspect of the present invention are represented by Formula III:

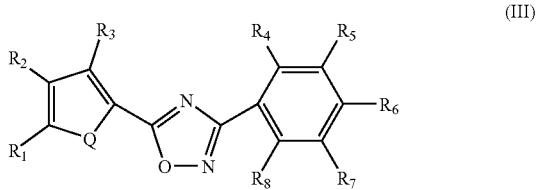

(III)

or a pharmaceutically acceptable salt, prodrug or tautomer thereof, wherein:

R$_1$-R$_8$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamino, hydroxy thiol, acyloxy, azido, alkoxy, aryloxy, heteroaryloxy, arylalkoxy, heteroarylalkoxy, haloalkoxy, carboxy, carbonylamido or alkylthiol, each of which is optionally substituted;

Q is S, O or NR$_9$, wherein R$_9$ is hydrogen, optionally substituted alkyl, optionally substituted cycloalkyl or optionally substituted aryl. Preferably R$_9$ is hydrogen, alkyl, cycloalkyl or aryl; more preferably, R$_9$ is hydrogen, alkyl or cycloalkyl.

Preferred compounds of Formula III include compounds wherein Q is S or O; and wherein R$_3$ is not a hydrogen.

Another group of preferred compounds of the present invention are represented by Formula IV:

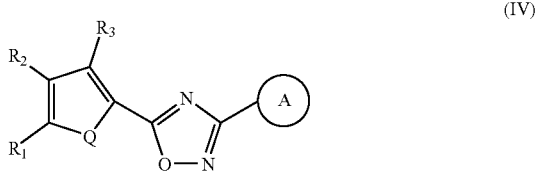

(IV)

and pharmaceutically acceptable salts, prodrugs and tautomers thereof, wherein:

R$_1$-R$_3$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamino, hydroxy, thiol, acyloxy, azido, alkoxy, aryloxy, heteroaryloxy, aryl alkoxy, heteroarylalkoxy, haloalkoxy, carboxy, carbonylamido or alkylthiol, each of which is optionally substituted;

Q is S, O or NR$_9$, wherein R$_9$ is hydrogen, optionally substituted alkyl, optionally substituted cycloalkyl or optionally substituted aryl. Preferably R$_9$ is hydrogen, alkyl, cycloalkyl or aryl; more preferably, R$_9$ is hydrogen, alkyl or cycloalkyl; and Ring A is an optionally substituted heterocycle or carbocycle.

Preferred compounds of Formula IV include compounds wherein ring A is morpholinyl, piperazinyl, piperidinyl or cyclohexyl.

Exemplary preferred compounds that may be employed in the method of the invention include, without limitation:

3-(3-Amino-4-chloro-phenyl)-5-(3-chlorothiophen-2-yl)-[1,2,4]-oxadiazole;

5-(3-Chlorothiophen-2-yl)-3-(3-dimethylamino-4-chloro-phenyl)-[1,2,4]-oxadiazole;

3-(3-Amino4-chloro-phenyl)-5-(3-bromofuran-2-yl)-[1,2,4]-oxadiazole;

5-(3-Bromofuran-2-yl)-3-(3-dimethylamino-4-chloro-phenyl)-[1,2,4]-oxadiazole;

N-{2-Chloro-5-[5-(3-chlorothiophen-2-yl)-[1,2,4]-oxadiazol-3-yl]-phenyl}-2-(4-methyl-piperazin-1-yl)-acetamide;

N-{2-Chloro-5-[5-(3-chlorothiophen-2-yl)-[1,2,4]-oxadiazol-3-yl]-phenyl}-succinamic acid ethyl ester;

5-(3-Chlorothiophen-2-yl)-3-(4-chloro-3-cyano-phenyl)-[1,2,4]-oxadiazole;

3-(4-Chloro-benzyloxy)-5-(3-chlorothiophen-2-yl)-[1,2,4]-oxadiazole;

5-(3-Chlorothiophen-2-yl)-3-(4-chloro-3-fluoro-phenyl)-[1,2,4]-oxadiazole;

5-(3-Chlorothiophen-2-yl)-3-(4-chloro-3-nitro-phenyl)-[1,2,4]-oxadiazole;

3-(5-Chloro-pyridin-2-yl)-5-(3-methoxy-thiophen-2-yl)-[1,2,4]-oxadiazole:

3-(5-Chloro-pyridin-2-yl)-5-(3-methyl-3H-imidazol-4-yl)-[1,2,4]-oxadiazole;

3-[2-(4-Chloro-phenyl)-vinyl]-5-(3-chlorothiophen-2-yl)-[1,2,4]-oxadiazole;

5-(3-Chloro-1H-pyrrol-2-yl)-3-(5-chloro-pyridin-2-yl)-[1,2,4]-oxadiazole;

3-(4-Chloro-phenyl)-5-(3-chloro-1H-pyrrol-2-yl)-[1,2,4]-oxadiazole;

5-(3-Chloro-1-methyl-1H-pyrrol-2-yl)-3-(4-chloro-phenyl)-[1,2,4]-oxadiazole;

5-[3-Chloro-1-(2-dimethylaminoethyl)-1H-pyrrol-2-yl]-3-(4-chloro-phenyl)-[1,2,4]-oxadiazole;

5-(3-Chlorothiophen-2-yl)-3-(1-piperidinyl)-[1,2,4]-oxadiazole;

5-(3-Chlorothiophen-2-yl)-3-(4-morpholinyl)-[1,2,4]-oxadiazole;

5-(3-Chlorothiophen-2-yl)-3-(morpholin4-yl)-[1,2,4]oxadiazole;

5-(3-Chlorothiophen-2-yl)-3-(pyrrolidin-1-yl)-[1,2,4]oxadiazole;

5-(3-Chlorothiophen-2-yl)-3-(4-methylpiperidin-1-yl)-[1,2,4]oxadiazole;

5-(3-Chlorothiophen-2-yl)-3-(2-methylpiperidin-1-yl)-[1,2,4]oxadiazole;

5-(3-Chlorothiophen-2-yl)-3-(4-trifluoromethylpiperidin-1-yl)-[1,2,4]oxadiazole;

5-(3-Chlorothiophen-2-yl)3-(4-methylpiperazin-1-yl)-[1,2,4]oxadiazole;

4-[5-(3-Chlorothiophene-2-yl)-[1,2,4]oxadiazol-3-yl]-piperazine-1-carboxylic acid benzyl ester;

4-[5-(3-Chlorothiophene-2-yl)-[1,2,4]oxadiazol-3-yl]-piperazine-1-carboxylic acid tert-butyl ester;

{1-[5-(3-Chlorothiophen-2-yl)-[1,2,4]oxadiazol-3-yl]-piperidin-4-yl}-carbamic acid tert butyl ester;
{1-[5-(3-Chlorothiophen-2-yl)-[1,2,4]oxadiazol-3-yl]-piperidin-4-yl}-acetic acid ethyl ester;
{1-[5-(3-Chlorothiophen-2-yl)-[1,2,4]oxadiazol-3-yl]-piperidin-3-yl}-acetic acid ethyl ester;
5-(3-Chlorothiophen-2-yl)-2-(piperidine-1-yl)-[1,3,4]oxadiazole;
5-(3-Chlorothiophen-2-yl)-2-(morpholin4-yl)-[1,3,4]oxadiazole;
5-(3-Chlorothiophen-2-yl)-2-(4-methylpiperazin-1-yl)-[1,3,4]oxadiazole;
4-[5-(3-Bromofuran-2-yl)-[1,2,4]oxadiazol-3-yl]-piperazine-1-carboxylic acid benzyl ester;
4-[5-(3-Bromofuran-2-yl)-[1,2,4]oxadiazol-3-yl]-piperazine-1-carboxylic acid tert-butyl ester;
5-(3-Chlorothiophen-2-yl)-2-(piperazin-1-yl)-[1,3,4]oxadiazole trifluoroacetic acid salt;
5-(3-Bromofuran-2-yl)-2-(piperazin-1-yl)-[1,3,4]oxadiazole trifluoroacetic acid salt;
5-(3-Chlorothiophen-2-yl)-3-(4-aminopiperidin-1-yl)-[1,2,4]oxadiazole trifluoroacetic acid salt;
5-(3-Chlorothiophen-2-yl)-3-(thiophen-2-yl)-[1,2,4]oxadiazole;
5-(3-Chlorothiophen-2-yl)-3-(1H-pyrrol-2-yl)-[1,2,4]oxadiazole;
5-(3-Chlorothiophen-2-yl)-3-(furan-2-yl)-[1,2,4]oxadiazole;
5-(3-Chlorothiophen-2-yl)-3-(furan-3-yl)-[1,2,4]oxadiazole;
3-(4-Chloro-2-methyl-phenyl)-5-(3-chlorothiophen-2-yl)-[1,2,4]oxadiazole;
5-(3-Chlorothiophen-2-yl)-3-(5-methylfuran-2-yl)-[1,2,4]oxadiazole;
5-(3-Chlorothiophen-2-yl)-3-(5-nitrofuran-2-yl)-[1,2,4]oxadiazole;
3-(4-Chloro-2-fluoro-phenyl)-5-(3-chlorothiophen-2-yl)-[1,2,4]oxadiazole;
5-(3-Chlorothiophen-2-yl)-3-(3-methyl-pyridin-2-yl)-[1,2,4]oxadiazole;
3-(4-Chloro-3-methyl-phenyl)-5-(3-chlorothiophen-2-yl)-[1,2,4]oxadiazole;
5-(3-Bromofuran-2-yl)-3-(4-chloro-2-methyl-phenyl)-[1,2,4]oxadiazole;
5-(3-Bromofuran-2-yl)-3-(5-chloro-3-methyl-pyridin-2-yl)-[1,2,4]oxadiazole;
{2-Chloro-5-[5-(3-chlorothiophene-2-yl)-[1,2,4]oxadiazol-3-yl]-phenylamino}-acetic acid ethyl ester;
N'-{2-Chloro-5-[5-(3-chlorothiophen-2-yl)-[1,2,4]oxadiazol-3-yl]-phenyl}-N,N-diethyl-ethane-1,2-diamine;
{2-Chloro-5-[5-(3-chlorothiophen-2-yl)-[1,2,4]oxadiazol-3-yl]-phenyl}-(2-morpholin4-yl-ethyl)-amine;
({2-Chloro-5-[5-(3-chlorothiophene-2-yl)-[1,2,4]oxadiazol-3-yl]-phenyl}-methylamino)-acetic acid ethyl ester;
({2-Chloro-5-[5-(3-chlorothiophene-2-yl)-[1,2,4]oxadiazol-3-yl]-phenyl}-methylamino)-acetic acid;
({2-Chloro-5-[5-(3-chlorothiophene-2-yl)-[1,2,4]oxadiazol-3-yl]-phenyl}-methylamino)-acetic acid N-hydroxysuccinimidyl ester;
5-(3-Bromofuran-2-yl)-3-(3-methyl-pyridin-2-yl)-[1,2,4]oxadiazole;
4-({2-Chloro-5-[5-(3-chlorothiophen-2-yl)-[1,2,4]oxadiazol-3-yl]-phenyl}-methyl-amino)-butyric acid methyl ester;
4-({2-Chloro-5-[5-(3-chlorothiophen-2-yl)-[1,2,4]oxadiazol-3-yl]-phenyl}-methyl-amino)-butyric acid;
4-({2-Chloro-5-[5-(3-chlorothiophen-2-yl)-[1,2,4]oxadiazol-3-yl]-phenyl}-methyl-amino)-butyric acid N-hydroxysuccinimidyl ester,
4-({2-Chloro-5-[5-(3-chlorothiophen-2-yl)-[1,2,4]oxadiazol-3-yl]-phenyl}-methyl-amino)-1-(4-methyl-piperazin-1-yl)-butan-1-one;
N-Butyl4({2-Chloro-5-[5-(3-chlorothiophen-2-yl)-[1,2,4]oxadiazol-3-yl]-phenyl}-methyl-amino)-butyramide;
4-({2-Chloro-5-[5-(3-chlorothiophen-2-yl)-[1,2,4]oxadiazol-3-yl]-phenyl}-methyl-amino)-butyric acid octyl ester;
{2-Chloro-5-[5-(3-chlorothiophen-2-yl)-[1,2,4]oxadiazol-3-yl]-phenyl}-ethyl-amine;
N-{2-Chloro-5-[5-(3-chlorothiophen-2-yl)-[1,2,4]oxadiazol-3-yl]-phenyl}-acetamide;
3-(3-Bromomethyl-4-chloro-phenyl)-5-(3-chlorothiophen-2-yl)-[1,2,4]oxadiazole;
3-(2-Bromomethyl-4-chloro-phenyl)-5-(3-chlorothiophen-2-yl)-[1,2,4]oxadiazole;
3-(4-Chloro-3-pyrrolidin-1-ylmethyl-phenyl)-5-(3-chlorothiophen-2-yl)-[1,2,4]oxadiazole;
3-(4-Chloro-3-dimethylaminomethyl-phenyl)-5-(3-chlorothiophen-2-yl)-[1,2,4]oxadiazole;
3-(4-Chloro-2-pyrrolidin-1-ylmethyl-phenyl)-5-(3-chlorothiophen-2-yl)-[1,2,4]oxadiazole; and
3-(4-Chloro-2-dimethylaminomethyl-phenyl)-5-(3-chlorothiophen-2-yl)-[1,2,4]oxadiazole;

and pharmaceutically acceptable salts or prodrugs thereof.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl groups mentioned above, which may be optionally substituted. Alkoxy substituents include, without limitation, halo, morpholino, amino including alkylamino and dialkylamino, and carboxy including esters therof.

Useful alkylthio groups include sulfur substituted by one of the $C_{1-10}$ alkyl groups mentioned above, which may be optionally substituted. Also included are the sulfoxides and sulfones of such alkylthio groups.

Useful amino groups include $-NH_2$, $-NHR_{15}$ and $-NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

Optional substituents on the alkyl, alkenyl, alkynyl, cycloalkyl, carbocyclic and heterocyclic groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl.

Optional substituents on the aryl, arylalkyl, arylalkenyl, arylalkynyl and heteroaryl and heteroarylalkyl groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy or carboxy.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are C3-8 cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted Useful arylalkoxy groups include benzyloxy and phenethyloxy.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups. e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroactoms.

Useful heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I-IV can be prepared as illustrated by the exemplary reaction in Scheme 1. Reaction of 3-chlorothiophene-2-carbonyl chloride with 3-amino-4-chlorobenzamidoxime in pyridine produced the product 3-(3-amino-4-chloro-phenyl)-5-(3-chlorothiophen-2-yl)-[1,2,4]-oxadiazole. Alternatively, the reaction also can be run in 1,4-dioxane followed by treatment with $BF_3OEt_2$, or in dioxane/pyridine, and produce the same oxadiazole product.

Scheme 1

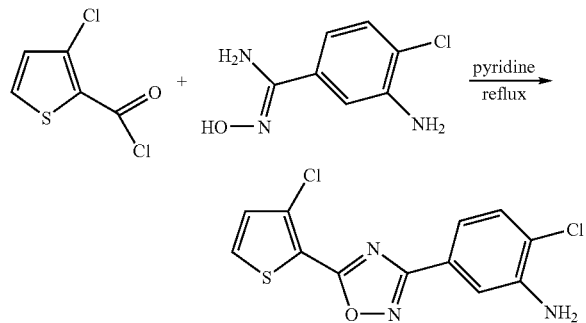

Compounds of this invention with Formulae I-IV may also be prepared as illustrated by the exemplary reaction in Scheme 2. Reaction of 1-piperidinecarbonitrile with hydroxylamine in ethanol produced the amidoxime intermediate, followed by reaction with 3-chlorothiophene-2-carbonyl chloride in refluxing pyridine to produce the product 5-(3-chlorothiophen-2-yl)-3-(1-piperidinyl)-[1,2,4]-oxadiazole.

Scheme 2

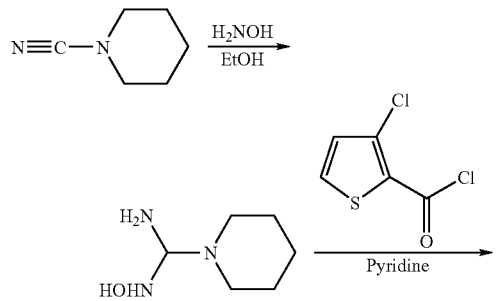

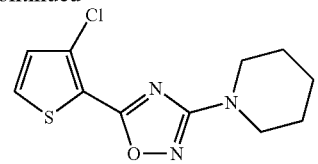

An important aspect of the present invention is the discovery that compounds having Formulae I-IV are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formulae I-IV are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer, such as breast cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I-IV, which functions as a caspase cascade activator and inducer of apoptosis.

The present invention also includes a therapeutic method comprising administering to an animal an effective amount of a compound, or a pharmaceutically acceptable salt or prodrug of said compound of Formulae I-IV, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic iymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

In another embodiment, a pharmaceutical composition comprising a compound, or a pharmaceutically acceptable salt of said compound of Formulae I-IV, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I-IV, which functions as a caspase cascade activator and inducer of apoptosis, in combination with at least one known cancer chemotherapeutic agent, or a pharmaceutically acceptable salt of said agent. Examples of known cancer chemotherapeutic agents which may be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; antibodies, such as campath, Herceptin® or Rituxan®. Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

It has been reported that alpha-1-adrenoceptor antagonists, such as doxazosin, terazosin, and tamsulosin can inhibit the growth of prostate cancer cell via induction of apoptosis (Kyprianou, N., et al., Cancer Res 60:4550-4555, (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known alpha-1-adrenoceptor antagonists, or a pharmaceutically acceptable salt of said agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., Cancer Res. 55: 408-413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., Cancer Res. 62:313-322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known sigma-2 receptor agonist, or a pharmaceutically acceptable salt of said agonist. Examples of known sigma-2 receptor agonists which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., Int. J. Cancer 97:746-750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin and cerivastatin.

It has been reported that HIV protease inhibitors, such as indinavir or saquinavir, have potent anti-angiogenic activities and promote regression of Kaposi sarcoma (Sgadari, C., et al., Nat. Med. 8:225-232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HIV protease inhibitor, or a pharmaceutically acceptable salt of said agent. Examples of known HIV protease inhibitors, which can be used for combination therapy include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., Cancer Chemother. Phamacol. 43:145-150 (1999)). 4HPR also was reported to have good activity in combination with gamma-radiation on bladder cancer cell lines (Zou, C., et al., Int. J. Oncol. 13:1037-1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylomithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., *Leukemia* 16:433-443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, such as STI571 (Imatinib mesilate, Gleevec), have potent synergetic effect in combination with other anti-leukemic agents, such as etoposide (Liu, W. M., et al. *Br. J. Cancer* 86:1472-1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known tyrosine kinase inhibitor, or a pharmaceutically acceptable salt of said agent. Examples of known tyrosine kinase inhibitors, which can be used for combination therapy include, but are not limited to, Gleevec®, ZD1839 (Iressa), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., *Clin. Cancer Res.* 7:3544-3550 (2001)). Synergy of the protein farnesyltransferase inhibitor SCH66336 and cisplatin in human cancer cell lines also has been reported (Adjei, A. A., et al., *Clin. Cancer. Res.* 7:1438-1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenyl-protein transferase inhibitors, which can be used for combination therapy include, but are not limited to, R115777, SCH66336, L-778, 123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209-4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known cyclin-dependent kinase inhibitor, or a pharmaceutically acceptable salt of said agent. Examples of known cyclin-dependent kinase inhibitor, which can be used for combination therapy include, but are not limited to, flavopiridol, UCN-01, roscovitine and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology* (Huntingt) 16(No. 4 Suppl. 3):17-21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known COX-2 inhibitor, or a pharmaceutically acceptable salt of said inhibitor. Examples of known COX-2 inhibitors which can be used for combination therapy include, but are not limited to, celecoxib, valecoxib, and rofecoxib.

Another embodiment of the present invention is directed to a composition effective to inhibit neoplasia comprising a bioconjugate of a compound described herein, which functions as a caspase cascade activator and inducer of apoptosis, in bioconjugation with at least one known therapeutically useful antibody, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-IV, which functions as a caspase cascade activator and inducer of apoptosis, is an effective treatment for autoimmune diseases.

Psoriasis is a chronic skin disease that is characterized by scaly red patches. Psoralen plus ultraviolet A (PUVA) is a widely used and effective treatment for psoriasis vulgaris. Coven, et al., *Photodennatol. Photoimmunol. Photomed.* 15:22-27 (1999), reported that lymphocytes treated with psoralen 8-MOP or TMP and UVA, displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dennatol. Res.* 290:240-245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I-IV, which functions as a caspase cascade activator and inducer of apoptosis, is an effective treatment for hyperproliferative skin diseases, such as psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119-128 (1998), found that although RA synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-IV, which functions as a caspase cascade activator and inducer of apoptosis, is an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-IV, which functions as a caspase cascade activator and inducer of apoptosis, is an effective treatment for inflammation.

Caspase cascade activators and inducers of apoptosis may also be a desirable therapy in the elimination of pathogens, such as HIV, Hepatitis C and other viral pathogens. The long lasting quiecence, followed by disease progression, may be explained by an anti-apoptotic mechanism of these pathogens leading to persistent cellular reservoirs of the virions. It has been reported that HIV-1infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis may serve as a beneficial host mechanism to limit the spread of HIV and new therapeutics using caspase/ apoptosis activators may be useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al. *Hepatology* 3:656-64 (2000)). Therefore, apoptosis inducers may be useful as therapeutics for HIV and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with antiproliferative properties are currently under clinical investigation, including actinomycin D, rapamycin or paclitaxel coated stents (Regar E., et al., *Br. Med. Bull.* 59:227-248 (2001)). Therefore, apoptosis inducers, which are antiproliferative, are useful as therapeutics for the prevention or reduction of in-stent restenosis.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated.

Preferably, approximately 0.01 to approximately 10 mg/kg of body weight is orally administered. For intramuscular injection, the dose is generally approximately one-half of the oral dose. For example, a suitable intramuscular dose would be approximately 0.0025 to approximately 25 mg/kg of body weight, and most preferably, from approximately 0.01 to approximately 5 mg/kg of body weight. If a known cancer chemotherapeutic agent is also administered, it is administered in an amount that is effective to achieve its intended purpose. The amounts of such known cancer chemotherapeutic agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 10 mg, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, and also preparations that may be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the compounds of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which may be used orally include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which may be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG-400), or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

3-(3-Amino-4-chloro-phenyl)-5-(3-chlorothiophen-2-yl)-[1,2,4]-oxadiazole a) 3-Amino-4-chloro-benzamidoxime: A solution of 3-amino-4-chloro-benzonitrile (1.37 g, 8.96 mmol) and 50 wt % hydroxylamine (1260 µL, 20.6 mmol) in ethanol (15.0 mL) was refluxed for 1 h. The solution was rotary evaporated to dryness and the residue was purified by flash column chromatography to yield 1.44 g (86%) of product as a white solid. $^1$H NMR (DMSO-$d_6$): 9.53 (s, 1H), 7.17 (d, J=8.24 Hz, 1H), 7.10 (d, J=1.92 Hz, 1H), 6.81 (dd, $J_{BA}$=8.38 Hz, $J_{BX}$=2.07, 1H), 5.64 (s, 2H), 5.36 (s, 2H).

b) 3-(3-Amino4-chloro-phenyl)-5-(3-chlorothiophen-2-yl)-[1,2,4]-oxadiazole: A solution of 3-amino-4-chloro-benzamidoxime (548 mg, 2.95 mmol) and 3-chlorothiophene-2-carbonyl chloride (535 mg, 2.95 mmol) in pyridine (3.0 mL) was stirred for 3 min under argon at ambient temperature. The solution was then heated to 118° C. over 20 min and refluxed for 30 min. The solution was cooled to room temperature and the product was precipitated by addition of 13 mL of deionized water. The precipitate was filtered in a Buchner funnel, washed with deionized water, and dried under vacuum to dryness. The product was purified by column chromatography (7:2 hexanes/ethylacetate) and by recrystallization (1:2 dichloromethane/hexanes) to yield 257 mg (36%) of the title compound as a white solid. $^1$H NMR (CDCl$_3$): 7.61 (d, J=5.22 Hz, 1H), 7.57 (d, J=1.92 Hz, 1H), 7.49 (dd, $J_1$=8.24 Hz, $J_2$=1.92 Hz, 1H), 7.37 (d, J=8.24 Hz, 1H), 7.13 (d, J=5.49 Hz, 1H), 4.22 (s, 2H).

EXAMPLE 2

5-(3-Chlorothiophen-2-yl)-3-(3-dimethylamino-4-chloro-phenyl)-[1,2,4]-oxadiazole A mixture of 3-(3-amino-4-chloro-phenyl)-5-(3-chlorothiophen-2-yl)-[1,2,4]-oxadiazole (75.5 mg, 0.242 mmol), sodium borohydride (54.4 mg, 1.44 mmol), and tetrahydrofuran (4.5 mL) was added to a stirred solution of 37 wt % formaldehyde solution (80 µL, 1.1 mmol), sulfuric acid (70 µL, 1.2 mmol), and tetrahydrofuran (1.5 mL). The solution was stirred at room temperature for 30 min, then methanol (2.5 mL) was added and the solution was stirred for 30 min. To the solution was added water (15 mL) and the solution was adjusted to pH 9 by addition of 3 M NaOH. The solution was extracted with ethyl acetate (60 mL). The ethyl acetate layer was dried over sodium sulfate and was rotary evaporated to dryness. The product was purified by column chromatography (7:2 hexanes/ethyl acetate) to yield 67.0 mg (81%) of the title compound as a white solid. $^1$H NMR (CDCl$_3$): 7.83 (d, J=1.92 Hz, 1H), 7.74 (dd, $J_1$=8.24 Hz, $J_2$=1.92 Hz, 1H), 7.61 (d, J=5.22 Hz, 1H), 7.48 (d, J=8.25 Hz, 1H), 7.14 (d, J=5.22 Hz, 1H), 2.90 (s, 6H).

EXAMPLE 3

3-(3-Amino4-chloro-phenyl)-5-(3-bromofuran-2-yl)-[1,2,4]-oxadiazole

The title compound was prepared from 3-amino-4-chloro-benzamidoxime (293 mg, 1.58 mmol) and 3-bromofuran-2- carbonyl chloride (329 mg, 1.57 mmol) in pyridine (2.8 mL) under reflux similar to Example 1b, yielded 289 mg (54%) as a white solid. $^1$H NMR (CDCl$_3$): 7.66 (d, J=1.64 Hz, 1H), 7.59 (d, J=1.92 Hz, 1H), 7.50 (dd, J$_1$=8.38 Hz, J$_2$=2.07 Hz, 1H), 7.37 (d, J=8.24 Hz, 1H), 6.75 (d, J=1.93 Hz, 1H), 4.22 (s, 2H).

EXAMPLE 4

5-(3-Bromofuran-2-yl)-3-(3-dimethylamino-4-chloro-phenyl)-[1,2,4]-oxadiazole

The title compound was prepared 3-(3-amino-4-chloro-phenyl)-5-(3-bromofuran-2-yl)-[1,2,4]-oxadiazole (275 mg, 0.809 mmol), sodium borohydride (185 mg, 4.88 mmol), 37 wt % formaldehyde solution (270 µL, 9.74 mmol), sulfuric acid (240 µL, 4.50 mmol), and tetrahydrofuran (22.0 mL), similar to Example 2, yielded 289 mg (54%) as a white solid. $^1$H NMR (CDCl$_3$): 7.85 (d, J=1.93 Hz, 1H), 7.76 (dd, J$_1$=8.24 Hz, J$_2$=2.20 Hz, 1H), 7.67 (d, J=1.93 Hz, 1H), 7.48 (d, J=8.24 Hz, 1H), 6.75 (d, J=1.92 Hz, 1H), 2.90 (s, 6H).

EXAMPLE 5

N-{2-Chloro-5-[5-(3-chlorothiophen-2-yl)-[1,2,4]-oxadiazol-3-yl]-phenyl}-2-(4-methyl-piperazin-1-yl)-acetamide A solution of 3-(3-amino-4-chloro-phenyl)-5-(3-chlorothiophen-2-yl)-[1,2,4]-oxadiazole (56.5 mg, 0.181 mmol), triethylamine (75.0 µL, 0.540 mmol), and bromo-acetyl bromide (48.0 µL, 0.549 mmol) and dichloromethane (15.0 mL) was stirred at room temperature for 30 min. The solution was washed with 5% hydrochloric acid solution, dried over sodium sulfate, and rotary evaporated to dryness. To the residue was added ethanol (10 mL), tetrahydrofuran (10 mL), and 1-methyl-piperazine (525 µL, 4.73 mmol) and the resulting solution was refluxed for 20 min under argon. The solution was partitioned between ethyl acetate (25 mL) and 10% sodium bicarbonate (15 mL). The ethyl acetate layer was washed with water (15 mL), dried over sodium sulfate and rotary evaporated to dryness to yield 68.7 mg (84%) of the title compound as a white solid. $^1$H NMR (CDCl$_3$): 10.04 (s, 1H), 9.25 (d, J=1.92 Hz, 1H), 7.85 (dd, J$_1$=8.24 Hz, J$_2$=1.64 Hz, 1H), 7.60 (d, J=5.22 Hz, 1H), 7.52 (d, J=8.24 Hz, 1H), 7.12 (d, J=5.49 Hz, 1H), 3.24 (s, 2H), 2.73 (s, 4H), 2.57 (s, 4H), 2.35 (s, 3H).

EXAMPLE 6

N-{2-Chloro-5-[5-(3-chlorothiophen-2-yl)-[1,2,4]-oxadiazol-3-yl]-phenyl}-succinamic acid ethyl ester The title compound was prepared from 3-(3-amino-4-chloro-phenyl)-5-(3-chlorothiophen-2-yl)-[1,2,4]-oxadiazole (107 mg, 0.343 mmol), triethylamine (960 µL, 6.91 mmol), and ethyl succinyl chloride (298.0 µL, 2.10 mmol) and dichloromethane (10.0 mL), similar to Example 5, yielded 112 mg (73%) as a white solid. $^1$H NMR (CDCl$_3$): 9.13 (s, 1H), 7.97 (s, 1H), 7.84 (dd, J$_1$=8.38 Hz, J$_2$=2.06 Hz, 1H), 7.60 (d, J=5.49 Hz, 1H), 7.51 (d, J=8.52 Hz, 1H), 7.12 (d, J=5.22 Hz, 1H), 4.19 (t, J=7.14 Hz, 2H), 2.79 (s, 4H), 1.28 (t, J=7.14 Hz, 3H).

EXAMPLE 7

5-(3-Chlorothiophen-2-yl)-3-(4-chloro-3-cyano-phenyl)-[1,2,4]-oxadiazole

A solution of sodium nitrite (76.8 mg, 1.11 mmol) and water (650 µL) was added dropwise to a stirred suspension of 3-(3-amino-4-chloro-phenyl)-5-(3-chlorothiophen-2-yl)-[1,2,4]-oxadiazole (335 mg, 1.07 mmol) in sulfuric acid (3.0 mL), water (8 mL) and some crushed ice in an ice bath. The solution was stirred for 1.25 h and then was poured into a solution of cuprous cyanide (152 mg, 1.70 mmol), potassium cyanide (231 mg, 3.55 mmol) and water (8 mL) in an ice bath. The solution was stirred for 10 min, then ethyl acetate (50 mL) was added, followed by sodium carbonate to bring the solution to pH 7, and the solution was equilibrated to room temperature. The ethyl acetate layer was concentrated by rotary evaporation and the product was purified by column chromatography to yield 75.7 mg (22%) of the title compound as a light yellow solid. $^1$H NMR (CDCl$_3$): 8.49 (d, J=2.20 Hz, 1H), 8.33 (dd, J$_1$=8.52 Hz, J$_2$=2.20 Hz, 1H), 7.67 (m, 2H), 7.16 (d, J=5.50 Hz, 1H).

EXAMPLE 8

3-(4-Chloro-benzyloxy)-5-(3-chlorothiophen-2-yl)-[1,2,4]-oxadiazole a) (3-Chlorothiophene-2-carbonyl)-thiocarbamic acid O-(4-chloro-benzyl) ester: 3-chlorothiophene-2-carbonyl-chloride (105.5 mg, 0.583 mmol) was added to a stirring solution of potassium thiocyanate (197.1 mg, 2.03 mmol) and acetone (10.0 mL), and the solution was stirred at room temperature for 30 min. The solution was filtered through Celite. To the filtrate was added 4-chlorobenzyl alcohol (257.0 mg, 1.80 mmol) and the solution was refluxed under argon for 23 h. The solution was cooled to room temperature and rotary evaporated to dryness. The product was purified by column chromatography (9:1 dichloromethane/ethyl acetate) to yield 63.2 mg (31%) as a white solid. $^1$H NMR (CDCl$_3$): 10.07 (s, 1H), 7.63 (d, J=5.49 Hz, 1H), 7.43 (d, J=8.24 Hz, 1H), 7.37 (d, J=8.52 Hz, 1H), 7.04 (d, J=5.49 Hz, 1H), 5.62 (s, 2H).

b) A stirred solution of (3-chlorothiophene-2-carbonyl)-thiocarbamic acid O-(4-chloro-benzyl) ester (52.3 mg, 0.151 mg), hydroxylamine hydrochloride (20.7 mg, 0.298 mmol) was refluxed under argon for 1 h. The solution was cooled to room temperature, then water (6 mL) was added to precipitate the product, and the mixture was filtered. The filter cake was dissolved in dichloromethane, filtered through glass wool, and rotary evaporated to dryness. The product was recrystallized from dichloromethane/methanol to yield 3.1 mg (6.2%) of the title compound as a white solid. $^1$H NMR (CDCl$_3$): 7.58 (d, J=5.7 Hz, 1H), 7.44 (d, J=8.4 Hz, 1H), 7.37 (d, J=8.4 Hz, 1H), 7.10 (d, J=5.1 Hz, 1H), 5.36 (s, 2H).

EXAMPLE 9

5-(3-Chlorothiophen-2-yl)-3-(4-chloro-3-fluoro-phenyl)-[1,2,4]-oxadiazole a) 4-Chloro-3-fluoro-benzamidoxime: The title compound was prepared from 4-chloro-3-fluoro-benzonitrile (4.90 g, 31.5 mmol), 50 wt % hydroxylamine (2.10 mL, 34.3 mmol), and ethanol (78 mL) similar to Example 1a, yielded 2.65 g (45%) as a white solid. $^1$H NMR (DMSO-d$_6$): 9.89 (s, 1H), 7.66 (dd, J$_1$=10.99 Hz, J$_2$=1.93 Hz, 1H), 7.60-7.54 (m, 2H), 5.97 (s, 2H).

b) 5-(3-Chlorothiophen-2-yl)-3-(4-chloro-3-fluoro-phenyl)-[1,2,4]-oxadiazole: The title compound was prepared from 4-chloro-3-fluoro-benzamidoxime (2.55 g, 13.5 mmol) and 3-chlorothiophene-2-carbonyl chloride (2.45 g, 13.5 mmol) in pyridine (17 mL), similar to Example 1b, yielded 4.17 g (98%) as a white solid. $^1$H NMR (CDCl$_3$): 7.98-7.89 (m, 2H), 7.63 (d, J=5.22 Hz, 1H), 7.54 (t, J=7.69 Hz, 1H), 7.14 (d, J=5.22 Hz, 1H).

EXAMPLE 10

5-(3-Chlorothiophen-2-yl)-3-(4-chloro-3-nitro-phenyl)-[1,2,4]-oxadiazole a) 4-Chloro-3-nitro-benzamidoxime: The title compound was prepared from 4-chloro-3-nitro-benzonitrile (5.14 g, 28.1 mmol), 50 wt % hydroxylamine;(1.90 mL, 31.0 mmol), tetrahydrofuran (36.0 mL) and ethanol (22.0 mL) similar to Example 1a, yielded 2.82 g (47%) as a white solid. $^1$H NMR (DMSO-d$_6$): 10.06 (s, 1H), 8.31 (dd, J$_1$=2.09 Hz, J$_2$=0.99 Hz, 1H), 7.98 (ddd, J$_1$=6.87 Hz, J$_2$=2.06 Hz, J$_3$=1.24 Hz, 1H), 7.80 (dd, J$_1$=8.52 Hz, J$_2$=0.82 Hz, 1H), 6.11 (s, 2H).

b) 5-(3-Chlorothiophen-2-yl)-3-(4-chloro-3-nitro-phenyl)-[1,2,4]-oxadiazole: The title compound was prepared from 4-chloro-3-nitro-benzamidoxime (2.76 g, 12.8 mmol) and 3-chlorothiophene-2-carbonyl chloride (2.32 g, 12.8 mmol) in pyridine (17.0 mL), similar to Example 1b, yielded 1.84 g (42%) as a white solid. $^1$H NMR (CDCl$_3$): 8.67 (d, J=1.92 Hz, 1H), 8.31 (dd, J$_1$=8.37 Hz, J$_2$=2.06 Hz, 1H), 7.71 (d, J=8.24 Hz, 1H), 7.66 (d, J=5.22 Hz, 1H), 7.16 (d, J=5.22 Hz, 1H).

EXAMPLE 11

3-(5-Chloro-pyridin-2-yl)-5-(3-methoxy-thiophen-2-yl)-[1,2,4]-oxadiazole a) 3-Methoxy-thiophene-2-carboxylic acid: A solution of lithium hydroxide (605 mg, 14.4 mmol) and water (10.0 mL) was added to a stirred solution of 3-methoxy-thiophene-2-carboxylic acid methyl ester (1.24 g, 7.22 mmol) and tetrahydrofuran (15.0 mL) and the solution was refluxed under argon for 3.5 h. The solution was cooled to room temperature and was partitioned between dichloromethane (50 mL) and 5% sodium bicarbonate solution (20 mL). The aqueous layer was adjusted to pH 3 with 10% hydrochloric acid solution and was extracted with ethyl acetate (2×50 mL). The ethyl acetate layer was dried over sodium sulfate and was concentrated to dryness by rotary evaporation to yield 876 mg (77%) as a white solid. $^1$H NMR (DMSO-d$_6$): 7.77 (d, J=5.22 Hz, 1H), 7.10 (d, J=5.49 Hz, 1H), 3.88 (s, 3H).

b) 3-Methoxy-thiophene-2-carboxylic acid 5-chloropyridine-2-amideoxime-O-ester: A solution of 5-chloropyridine-2-amidoxime (100.9 mg, 0.588 mmol), 3-methoxy-thiophene-2-carboxylic acid (112 mg, 0.707 mmol), 1-(3-dimethylaminopropyl)-3-ethylcarbodiimide (135.1 mg, 0.705 mmol), 4-dimethylamino-pyridine (89.3 mg, 0.731 mmol), and dichloromethane (15.0 mL) was stirred at room temperature for 5 h. The solution was washed with saturated sodium bicarbonate solution (20 mL) and water (20 mL). The dichlromethane layer was rotary evaporated to dryness and the product was purified by column chromatography (9:1 dichloromethane/ethyl acetate) to yield 161 mg (88%) of the product as a white solid. $^1$H NMR (CDCl$_3$): 8.54 (dd, J$_1$=2.33 Hz, J$_2$=0.69 Hz, 1H), 8.23 (dd, J$_1$=8.51 Hz, J$_2$=0.82 Hz, 1H), 7.75 (dd, J$_1$=8.52 Hz, J$_2$=2.19 Hz, 1H), 7.52 (d, J=5.50 Hz, 1H), 6.92 (d, J=5.49 Hz, 1H), 6.13 (s broad, 2H), 4.04 (s, 3H).

c) 3-(5-Chloro-pyridin-2-yl)-5-(3-methoxy-thiophen-2-yl)-[1,2,4]-oxadiazole: A stirred solution of 3-methoxy-thiophene-2-carboxylic acid 5-chloropyridine-2-amidoxime-O-ester (102.0 mg, 0.327 mmol) and pyridine (1.5 mL) in a sealed tube was heated to 180° C. with microwaves for 13 min. The product was rotary evaporated to dryness at 40° C. and was purified by column chromatography (95:5 dichloromethane/ethyl acetate) to yield 54.4 mg (57%) of the title compound as a white solid. $^1$H NMR (CDCl$_3$): 8.76 (dd, J$_1$=2.47 Hz, J$_2$=0.83 Hz, 1H), 8.16 (dd, J$_1$=8.38 Hz, J$_2$=0.68 Hz, 1H), 7.83 (dd, J$_1$=8.51 Hz, J$_2$=2.47 Hz, 1H), 7.57 (d, J=5.50 Hz, 1H), 6.96 (d, J=5.49 Hz, 1H), 4.09 (s, 3H).

EXAMPLE 12

3-(5-Chloro-pyridin-2-yl)-5-(3-methyl-3H-imidazol-4-yl)-[1,2,4]-oxadiazole

A mixture of 3-methyl-3H-imidazole-4-carbonyl chloride (91 mg, 0.5 mmol), 5-chloro-N-hydroxy-pyridine-2-carboxamidine (85.8 mg, 0.5 mmol) in pyridine (5 ml) was refluxed for 4 h and then cooled to room temperature. To the solution was added water (20 ml) and the product precipitated from the solution. The solid was collected by filtration and washed with water, dried to give 6 mg (5%) of the title compound. $^1$H NMR (CDCl$_3$): 8.78 (d, J=2.4 Hz, 1H), 8.15 (d, J=8.4 Hz, 1H), 8.05 (s, 1H), 7.87 (dd, J=2.7 Hz, J=8.7 Hz, 1H), 7.70 (s, 1H), 4.14 (s, 3H).

EXAMPLE 13

3-[2-(4-Chloro-phenyl)-vinyl]-5-(3-chlorothiophen-2-yl)-[1,2,4]-oxadiazole

A solution of 3-(4-chloro-phenyl)-acrylonitrile (1.63 g, 10 mmol) and hydroxyamine (0.74 ml, 12 mmol) in ethanol (10 ml) was stirred at room temperature overnight. The solvent was evaporated, and the residue was purified by column chromatography (EtOAc:Hexane=1:3) to give 1.0 g (51%) of 3-(4-chloro-phenyl)-N-hydroxy-acrylamidine.

The title compound was prepared similar to Example 12. From 3-chlorothiophene-2-carbonyl chloride (138.2 mg, 0.76 mmol) and 3-(4-chloro-phenyl)-N-hydroxy-acrylamidine (150 mg, 0.76 mmol) was obtained 24 mg (10%) of the title compound. $^1$H NMR (CDCl$_3$): 7.74 (d, J=15.9 Hz, 1H), 7.61 (d, J=5.1 Hz, 1H), 7.54-7.51 (m, 2H), 7.39 (d, J=8.7 Hz, 2H), 7.14-7.05 (m, 2H).

EXAMPLE 14

5-(3-Chloro-1H-pyrrol-2-yl)-3-(5-chloro-pyridin-2-yl)-[1,2,4]-oxadiazole

The title compound was prepared similar to Example 12. From 3-chloro-1H-pyrrole-2-carbonyl chloride (282.2 mg, 1.72 mmol) and 5-chloro-N-hydroxy-pyridine-2-carboxamidine (295 mg, 1.72 mmol) was obtained 29 mg (6%) of the title compound. $^1$H NMR (CDCl$_3$): 9.68 (brs, 1H), 8.77 (d, J=2.1 Hz, 1H), 8.16 (d, J=8.4 Hz, 1H), 7.86 (dd, J=8.4 Hz, J=2.4 Hz, 1H), 7.03-7.01 (m, 1H), 6.39-6.37 (m, 1H).

EXAMPLE 15

3-(4-Chloro-phenyl)-5-(3-chloro-1H-pyrrol-2-yl)-[1,2,4]-oxadiazole

The title compound was prepared similar to Example 12. From 3-chloro-1H-pyrrole-2-carbonyl chloride (856.4 mg, 5.22 mmol) and 4-chloro-N-hydroxy-benzamidine (890.5 mg, 5.22 mmol) was obtained 418 mg (28.6%) of the title compound. $^1$H NMR (CDCl$_3$): 9.41 (brs, 1H), 8.06-8.03 (m, 2H), 7.47-7.45 (m, 2H), 7.00 (t, J=3.0 Hz, 1H), 6.37 (t, J=3.0 Hz, 1H).

EXAMPLE 16

5-(3-Chloro-1-methyl-1H-pyrrol-2-yl)-3-(4-chloro-phenyl)-[1,2,4]-oxadiazole

A mixture of 3-(4-chloro-phenyl)-5-(3-chloro-1H-pyrrol-2-yl)-[1,2,4]-oxadiazole (30.0 mg, 0.11 mmol), iodomethane (0.08 ml, 0.17 mmol) and potassium carbonate (23 mg, 0.17 mmol) in dimethylformamide (2 ml) was heated at 85° C. for 4 h. It was diluted by water (20 ml) and the mixture was extracted by EtOAc. The extracts were evaporated, and the residue was purified by column chromatography (EtOAc:Hexane=1:1) to give 12.0 mg (37%) of the title compound. $^1$H NMR (CDCl$_3$): 8.11-8.07 (m, 2H), 7.50-7.45 (m, 2H), 6.84 (d, J=3.0 Hz, 1H), 6.28 (d, J=3.3 Hz, 1H), 4.08 (s, 3H).

EXAMPLE 17

5-[3-Chloro-1-(2-dimethylaminoethyl)-1H-pyrrol-2-yl]-3-(4-chloro-phenyl)-[1,2,4]-oxadiazole The title compound was prepared similar to Example 16. From 3-(4-chloro-phenyl)-5-(3-chloro-1H-pyrrol-2-yl)-[1,2,4]-oxadiazole (48.0 mg, 0.17 mmol), 2-dimethylaminoethyl chloride hydrochloride (37 mg, 0.26 mmol) and potassium carbonate (35.5 mg, 0.26 mmol) was obtained 4 mg (7.0%) of the title compound $^1$H NMR (CDCl$_3$): 8.08 (d, J=8.7 Hz, 2H), 7.48 (d, J=8.7 Hz, 2H), 6.96 (d, J=2.7 Hz, 1H), 6.29 (d, J=2.7 Hz, 1H), 4.59 (t, J=6.9 Hz, 2H), 2.69 (t, J=6.9 Hz, 2H), 2.30 (s, 6H).

EXAMPLE 18

5-(3-Chlorothiophen-2-yl)-3-(1-piperidinyl)-[1,2,4]-oxadiazole a) N-Hydroxy-piperidine-1-carboxamidine To a flame-dried 100 mL round bottom reaction flask charged with a magnetic stir bar, under argon, at room temperature was added 1-piperidinecarbonitrile (1.00 g, 9.07 mmol) and anhydrous ethanol (18 mL). After 10 minutes, hydroxylamine (0.61 mL, 9.9 mmol, 50% wt/water) was added to the stirring clear solution and the solution was then heated to 80° C. The clear solution was heated at 80° C. for 1.5 h, cooled to room temperature, and then concentrated in vacuo to a clear oil. The crude amidoxime material was carried on without further purification.

b) 5-(3-Chlorothiophen-2-yl)-3-(1-piperidinyl)-[1,2,4]-oxadiazole. To a flame-dried sealed reaction flask charged with a magnetic stir bar was added the crude amidoxime (0.171 g, 1.19 mmol), 3-chlorothiophene-2-carbonyl chloride (0.216 g, 1.19 mmol) and pyridine (2.4 mL). The viscous solution became a yellow solution upon being heated to 120° C. The yellow solution was heated at 120° C. for 1 h and then cooled to room temperature and stirred overnight. The reaction solution was diluted with ethyl acetate (50 mL), washed with 1M HCl (3×20 mL), NaHCO$_3$ (2×20 mL), brine (15 mL), dried over MgSO$_4$, filtered and concentrated to yield a yellow residue. Purification by column chromatography (elution with EtOAc:hexanes, 1:2) yielded 0.022 g (6.8%) of a yellow solid: $^1$H NMR (CDCl$_3$) 7.51 (d, 1H, J=5.22), 7.05 (d, 1H, J=5.22 Hz), 3.46 (m, 4H), 1.65 (m, 6H).

EXAMPLE 19

5-(3-Chlorothiophen-2-yl)-3-(4-morpholinyl)-[1,2,4]-oxadiazole (a) N-Hydroxy-morpholine-4-carboxamidine. The title compound was prepared from 4-morpholinecarbonitrile and hydroxylamine by a procedure similar to Example 18a in 99% yield. $^1$H-NMR (CDCl$_3$) 4.36 (br s, 2H), 3.72 (m, 4H), 3.09 (m, 4H).

(b) 5-(3-Chlorothiophen-2-yl)-3-(4-morpholinyl)-[1,2,4]-oxadiazole. The title compound was prepared from N-hydroxy-morpholine-4-caboxamidine, 3-chlorothiophene-2-carbonyl chloride and pyridine by a procedure similar to Example 18b in 49% yield. $^1$H-NMR (CDCl$_3$) 7.53 (dd, 1H, J=5.22 and 0.55 Hz), 7.07 (dd, 1H, J=5.22 and 0.55 Hz), 3.82 (m, 4H), 3.51 (m, 4H).

EXAMPLE 20

5-(3-Chlorothiophen-2-yl)-3-(morpholin4-yl)-[1,2,4]oxadiazole (a) N-Hydroxy-morpholine4-carboxamidine. The title compound was prepared in a manner similar to Example 18a. From 4-morpholinecarbonitrile (1.00 g, 8.92 mmol), EtOH (17.8 mL) and hydroxylamine (0.600 mL, 9.81 mmol, 50% wt/water) was obtained 1.24 g (96%) of the title compound as a white solid. $^1$H NMR (CDCl$_3$): 4.36 (br s, 2H), 3.72 (t, 4H, J=4.8 Hz), 3.09 (t, 4H, J=4.8 Hz).

(b) 5-(3-Chlorothiophen-2-yl)-3-(morpholin-4-yl)-[1,2,4]oxadiazole. The title compound was prepared in a manner similar to Example 18b. From N-hydroxy-morpholine-4-carboxamidine (0.172 g, 1.19 mmol), 3-chlorothiophene-2-carbonyl chloride (0.216 g, 1.19 mmol) and pyridine (2.4 mL) was obtained 0.160 g (49%) of the title compound as a white solid. $^1$H NMR (CDCl$_3$): 7.54 (dd, 1H, J=5.4 and 0.7 Hz), 7.08 (dd, 1H, J=5.4 and 0.7 Hz), 3.83-3.80 (m, 4H), 3.53-3.50 (m, 4H).

EXAMPLE 21

5-(3-Chlorothiophen-2-yl)-3-(pyrrolidin-1-yl)-[1,2,4]oxadiazole (a) Pyrrolidine-1-carbonitrile. To a clear solution of pyrrolidine (0.500 g, 7.03 mmol), anhydrous THF (23 mL) and anhydrous Et$_3$N (0.99 mL, 7.03 mmol) at 0° C. was added cyanogen bromide (0.744 g, 7.03 mmol) in one portion. The resulting white suspension was stirred at 0° C. for 2 h, then equilibrated to room temperature and stirred for 48 h. The solvent was evaporated and the white solid was diluted with ethyl acetate (100 mL), washed with water (2×20 mL), brine (15 mL), dried over MgSO$_4$, filtered and concentrated to give 0.67 g (100%) of the title compound as a yellow oil. $^1$H NMR (CDCl$_3$): 3.42-3.64 (m, 4H), 1.94-1.88 (m, 4H).

(b) N-Hydroxy-pyrrolidine-1-carboxamidine. The title compound was prepared in a manner similar to Example 18a. From pyrrolidine-1-carbonitrile (0.670 g, 6.96 mmol), hydroxylamine (0.253 mL, 7.66 mmol, 50% wt/water) was obtained 0.662 g (74%) of the title compound as a yellow oil. $^1$H NMR (CDCl$_3$): 4.62-4.55 (br s, 2H), 3.24-3.20 (m, 4H), 1.90-1.85 (m, 4H).

(c) 5-(3-Chlorothiophen-2-yl)-3-(pyrrolidin-1-yl)-[1,2,4]oxadiazole. The title compound was prepared in a manner similar to Example 18b. From N-hydroxy-pyrrolidine-1-carboxamidine (0.041 g, 0.32 mmol), 3-chlorothiophene-2-carbonyl chloride (0.057 g, 0.32 mmol) and anhydrous pyridine (1.0 mL) was obtained 0.006 g (7%) of the title compound as a white solid. $^1$H NMR (CDCl$_3$): 7.52-7.50 (m, 1H), 7.07-7.05 (m, 1H), 3.52-3.47 (m, 4H), 2.02-1.97 (m, 4H).

Compounds of Examples 22-30 were prepared by a procedure similar to that of Example 21 in three steps started from the corresponding amine and cyanogen bromide.

EXAMPLE 22

5-(3-Chlorothiophen-2-yl)-3-(4-methylpiperidin-1-yl)-[1,2,4]oxadiazole (a) 4-Methyl-piperidine-1-carbonitrile. $^1$H NMR (CDCl$_3$): 3.42-3.36 (m, 2H), 3.05-2.95 (m, 2H), 1.69-1.64 (m, 2H), 1.51-1.45 (m, 1H), 1.37-1.29 (m, 2H), 0.97 (d, 3H, J=6.3 Hz).

(b) N-Hydroxy-4-methylpiperidine-1-carboxamidine. $^1$H NMR (CDCl$_3$): 4.584.51 (br s, 2H), 3.55-3.51 (m, 2H), 2.64-2.56 (m, 2H), 1.63-1.59 (m, 4H), 1.45-1.41 (m, 1H), 1.22-1.20 (m, 3H).

(c) 5-(3-Chlorothiophen-2-yl)-3-(4-methylpiperidin-1-yl)-[1,2,4]oxadiazole. $^1$H NMR (CDCl$_3$): 7.51 (d, 1H, J=5.5 Hz), 7.06 (d, 1H, J=5.5 Hz), 4.06-4.02 (m, 2H), 2.98-2.89 (m, 2H), 1.72-1.58 (m, 3H), 1.30-1.24 (m, 2H), 0.98 (d, 3H, J=6.3 Hz).

EXAMPLE 23

5-(3-Chlorothiophen-2-yl)-3-(2-methylpiperidin-1-yl)-[1,2,4]oxadiazole (a) 2-Methyl-piperidine-1-carbonitrile. $^1$H NMR (CDCl$_3$): 3.42-3.41 (m, 1H), 3.07-2.99 (m, 2H), 1.84-1.80 (m, 1H), 1.72-1.61 (m, 3H), 1.35-1.25 (m, 5H).

(b) N-Hydroxy-2-methylpiperidine-1-carboxamidine. $^{13}$C NMR (CDCl$_3$, E/Z isomers, 2 extra peaks): 158.4, 156.4, 57.7, 49.5, 46.4, 41.4, 38.8, 30.6, 29.9, 25.4, 25.3, 19.3, 18.3, 18.2, 15.4, 13.9.

(c) 5-(3-Chlorothiophen-2-yl)-3-(2-methylpiperidin-1-yl)-[1,2,4]oxadiazole. $^1$H NMR (CDCl$_3$): 7.50 (d, 1H, J=5.5 Hz), 7.05 (d, 1H, J=5.2 Hz), 4.39-4.34 (m, 1H), 3.89-3.83 (m, 1H), 3.10 (dt, 1H, J=12.4 and 3.0 Hz), 1.80-1.59 (m, 6H), 1.22 (d, 3H, J=6.9 Hz).

EXAMPLE 24

5-(3-Chlorothiophen-2-yl)-3-(4-trifluoromethylpiperidin-1-yl)-[1,2,4]oxadiazole (a) 4-Trifluoromethyl-piperidine-1-carbonitrile. $^1$H NMR (CDCl$_3$): 3.56-3.50 (m, 2H), 3.09-3.04 (m, 3H), 2.20-2.12 (m, 1H), 1.96-1.90 (m, 2H), 1.80-1.65 (m, 2H), 1.30-1.25 (m, 1H).

(b) N-Hydroxy-4-trifluoromethyl-piperidine-1-carboxamidine. $^1$H NMR (CDCl$_3$): 4.29 (br s, 2H), 3.71-3.66 (m, 2H), 2.67-2.58 (m, 2H), 2.17-2.10 (m, 1H), 1.88-1.84 (m, 2H), 1.67-1.53 (m, 3H), 1.19-1.10 (m, 1H).

(c) 5-(3-Chlorothiophen-2-yl)-3-(4-trifluoromethylpiperidin-1-yl)-[1,2,4]oxadiazole. $^1$H NMR (CDCl$_3$): 7.53 (d, 1H, J=5.2 Hz), 7.07 (d, 1H, J=5.5 Hz), 4.21 (d, 2H, J=12.9 Hz), 2.95 (dt, 2H, J=12.8 and 2.5 Hz), 2.30-2.22 (m, 1H), 1.96 (d, 2H, J=12.6 Hz), 1.68 (ddd, 2H, J=12.9, 12.6, 4.4 and 4.1 Hz).

EXAMPLE 25

5-(3-Chlorothiophen-2-yl)-3-(4-methylpiperazin-1-yl)-[1,2,4]oxadiazole (a) 4-Methyl-piperazine-1-carbonitrile. $^1$H NMR (CDCl$_3$): 3.26 (t, 4H, J=5.1 Hz), 2.47 (t, 4H, J=5.1 Hz), 2.31 (d, 3H, J=0.9 Hz).

(b) N-Hydroxy-4-methyl-piperazine-1-carboxamidine. $^1$H NMR (CDCl$_3$): 4.39 (br s, 2H), 3.44-3.42 (m, 1H), 3.15-3.12 (m, 3H), 2.45-2.39 (m, 4H), 2.30-2.27 (m, 3H).

(c) 5-(3-Chlorothiophen-2-yl)-3-(4-methylpiperazin-1-yl)-[1,2,4]oxadiazole. $^1$H NMR (CDCl$_3$): 7.98 (d, 1H, J=5.5 Hz), 7.26 (d, 1H, J=5.2 Hz), 3.48-3.44 (m, 4H, J=5.2 and 5.0 Hz), 2.447-2.44 (m, 4H, J=5.2 and 5.0 Hz), 2.27 (s, 3H).

EXAMPLE 26

4-[5-(3-Chlorothiophene-2-yl)-[1,2,4]oxadiazol-3-yl]-piperazine-1-carboxylic acid benzyl ester (a) 4-Cyano-piperazine-1-carboxylic acid benzyl ester. $^1$H NMR (CDCl$_3$): 7.35 (m, 5H), 5.14 (s, 2H), 3.62-3.59 (m, 4H), 3.23-3.21 (m, 4H).

(b) 4-(N-Hydroxycarbamimidoyl)-piperazine-1-carboxylic acid benzyl ester. $^1$H NMR (DMSO-d$_6$): 8.37 (s, 1H), 7.38-7.36 (m, 5H), 5.21 (br s, 2H), 5.08 (s, 2H), 3.41-3.39 (m, 4H), 2.98-2.95 (m, 4H).

(c) 4-[5-(3-Chlorothiophene-2-yl)-[1,2,4]oxadiazol-3-yl]-piperazine-1-carboxylic acid benzyl ester. $^1$H NMR (CDCl$_3$): 7.54 (d, 1H, J=5.2 Hz), 7.39-7.33 (m, 5H), 7.07 (d, 1H, J=5.2 Hz), 5.17 (s, 2H), 3.65-3.62 (m, 4H), 3.52 (m, 4H).

EXAMPLE 27

4-[5-(3-Chlorothiophene-2-yl)-[1,2,4]oxadiazol-3-yl]-piperazine-1-carboxylic acid tert-butyl ester (a) 4-Cyano-piperazine-1-carboxylic acid tert-butyl ester. $^1$H NMR (CDCl$_3$): 3.53 (t, 4H, J=5.1 Hz), 3.20 (t, 4H, J=5.1 Hz), 1.46 (s, 9H).

(b) 4-(N-Hydroxycarbamimidoyl)-piperazine-1-carboxylic acid t-butyl ester. $^1$H NMR (DMSO-d$_6$): 8.35 (s, 1H), 5.19 (s, 2H), 3.33-3.28 (m, 4H), 2.94-2.91 (m, 4H), 1.40 (s, 9H).

(c) 4-[5-(3-Chlorothiophene-2-yl)-[1,2,4]oxadiazol-3-yl]-piperazine-1-carboxylic acid tert-butyl ester. $^1$H NMR (CDCl$_3$): 7.53 (dd, 1H, J=5.2 and 1.1 Hz), 7.07 (dd, 1H, J=5.2 and 1.1 Hz), 3.55-3.51 (m, 8H), 1.48 (s, 9H).

EXAMPLE 28

{1-[5-(3-Chlorothiophen-2-yl)-[1,2,4]oxadiazol-3-yl]-piperidin-4-yl}-carbamic acid tert butyl ester (a) (1-Cyano-piperidin-4-yl)-carbamic acid tert butyl ester. $^1$H NMR (CDCl$_3$): 4.52 (br s, 1H), 3.57-3.52 (m, 1H), 3.45-3.41 (m, 2H), 3.13-3.04 (m, 2H), 2.00-1.96 (m, 2H), 1.56-1.44 (m, 1H).

(b) [1-(N-Hydroxycarbamimidoyl)-piperidin4-yl]-carbamic acid t-butyl ester. $^1$H NMR (DMSO-d$_6$): 8.21 (s, 1H), 6.81 (d, 1H, J=6.9 Hz), 5.08 (s, 2H), 1.63-1.61 (m, 2H), 1.37-1.31 (m, 11H).

(c) {1-[5-(3-Chlorothiophen-2-yl)-[1,2,4]oxadiazol-3-yl]-piperidin-4-yl}-carbamic acid tert butyl ester. $^1$H NMR (DMSO-d$_6$): 8.10 (d, 1H, J=5.2 Hz), 7.35 (d, 1H, J=5.2 Hz), 6.90 (d, 1H, J=7.4 Hz), 3.83 (d, 2H, J=12.1 Hz), 3.48 (m, 1H), 3.03 (m, 2H, J=11.8 and 10.7 Hz), 1.80 (d, 2H, J=12.1 Hz), 1.39 (s, 9H).

EXAMPLE 29

{1-[5-(3-Chlorothiophen-2-yl)-[1,2,4]oxadiazol-3-yl]-piperidin-4-yl}-acetic acid ethyl ester (a) (1-Cyano-piperidin-4-yl)-acetic acid ethyl ester. $^1$H NMR (CDCl$_3$): 4.14 (q, 2H, J=7.1 Hz), 3.44-3.39 (m, 2H), 3.09-3.04 (m, 2H), 2.27-2.24 (m, 2H), 1.94-1.90 (m, 1H), 1.79-1.74 (m, 2H), 1.42-1.36 (m, 2H), 1.26 (t, 3H, J=7.1 Hz).

(b) [1-(N-Hydroxycarbamimidoyl)-piperidin-4-yl]-acetic acid ethyl ester. $^1$H NMR (DMSO-d$_6$): 5.16-5.14 (br s, 2H), 4.05 (q, 2H, J=7.1 Hz), 3.56-3.50 (m, 2H), 3.07 (q, 1H, J=7.1 Hz), 2.47-2.42 (m, 1H), 2.22-2.20 (m, 2H), 1.78-1.72 (m, 1H), 1.61-1.57 (m, 2H), 1.09-0.96 (m, 5H).

(c) {1-[5-(3-Chlorothiophen-2-yl)-[1,2,4]oxadiazol-3-yl]-piperidin-4-yl}-acetic acid ethyl ester. $^1$H NMR (CDCl$_3$): 7.52 (dd, 1H, J=5.2 and 0.8 Hz), 7.06 (dd, 1H, J=5.5 and 0.8 Hz), 4.16 (q, 2H, J=7.1 Hz), 4.07 (dd, 2H, J=10.9 and 2.3 Hz), 2.98 (td, 2H, J=12.7 and 2.8 Hz), 2.28 (d, 2H, J=6.9 Hz), 2.03 (m, 1H), 1.80 (d, 2H), 1.35 (m, 2H), 1.27 (t, 3H, J=7.1 Hz).

EXAMPLE 30

{1-[5-(3-Chlorothiophen-2-yl)-[1,2,4]oxadiazol-3-yl]-piperidin-3-yl}-acetic acid ethyl ester (a) (1-Cyano-piperidin-3-yl)-acetic acid ethyl ester. $^{13}$C NMR (CDCl$_3$): 171.2, 118.0, 60.6, 54.1, 49.7, 45.9, 37.9, 31.9, 29.3, 23.7, 14.2, 12.9.

(b) [1-(N-Hydroxycarbamimidoyl)-piperidin-3-yl]-acetic acid ethyl ester. $^1$H NMR (DMSO-d$_6$): 5.06 (s, 2H), 4.05 (q, 2H, J=7.1 Hz), 3.04 (q, 1H, J=7.1 Hz), 2.47-2.43 (m, 1H), 2.27-2.16 (m, 3H), 1.89-1.85 (m, 1H), 1.73-1.69 (m, 1H), 1.56-1.44 (m, 2H), 1.20-1.15 (m, 3H), 1.08-0.95 (m, 2H).

(c) {1-[5-(3-Chlorothiophen-2-yl)-[1,2,4]oxadiazol-3-yl]-piperidin-3-yl}-acetic acid ethyl ester. $^1$H NMR (CDCl$_3$): 7.52 (d, 1H, J=5.2 Hz), 7.06 (d, 1H, J=5.2 Hz), 4.16 (q, 2H, J=7.1 Hz), 4.01-3.89 (m, 2H), 3.05-2.96 (m, 1H), 2.79 (dd, 1H, J=12.6 and 9.9 Hz), 2.36-2.15 (m, 3H), 1.94-1.89 (m, 1H), 1.75-1.64 (m, 1H), 1.28 (t, 3H, J=7.1 Hz).

EXAMPLE 31

5-(3-Chlorothiophen-2-yl)-2-(piperidine-1-yl)-[1,3,4]oxadiazole (a) 3-Chlorothiophene-2-carboxylic acid hydrazide. To a solution of hydrazine (0.860 mL, 27.6 mmol) at 0° C. was added a clear solution of 3-chlorothiophene-2-carbonyl chloride (1.00 g, 5.52 mmol) and CH$_2$Cl$_2$ (11.0 mL). The reaction was stirred at 0° C. for 0.5 h and then equilibrated to room temperature. The solvent was evaporated and the yellow solid was diluted with ethyl acetate (70 mL), washed with water (2×20 mL), dried over MgSO$_4$, filtered and concentrated to give 0.80 g (82%) of the title compound as a white solid. $^1$H NMR (CDCl$_3$): 9.41 (s, 1H), 7.81 (d, 1H, J=5.2 Hz), 7.13 (d, 1H, J=5.5 Hz), 4.57 (s, 2H).

(b) Piperidine-1-carboxylic acid N-(3-chlorothiophene-2-carbonyl)-hydrazide. A yellow solution of 3-chlorothiophene-2-carboxylic acid hydrazide (0.150 g, 0.852 mmol), THF (1.7 mL) and Et$_3$N (0.12 mL, 0.852 mmol) was cooled to 0° C. and 1-piperidinecarbonyl chloride (0.106 mL, 0.852 mmol) was added dropwise. The yellow solution was equilibrated to room temperature and stirred for 18 h The reaction solution was diluted with water (20 mL) and then extracted with ethyl acetate (30 mL). The organic layer was washed with water (15 mL), brine (10 mL), dried over MgSO$_4$, and then concentrated to yield 0.210 g (86%) of the title compound as a white solid. $^1$H NMR (CDCl$_3$): 9.29 (d, 1H, J=5.2 Hz), 7.51-7.48 (m, 2H), 7.00 (d, 1H, J=5.2 Hz), 3.45-3.43 (m, 4H), 1.64-1.60 (m, 6H).

(c) 5-(3-Chlorothiophen-2-yl)-2-(piperidine-1-yl)-[1,3,4]oxadiazole. A yellow solution of piperidine-1-carboxylic acid N-(3-chlorothiophene-2-carbonyl)-hydrazide (0.100 g, 0.347 mmol) and thionyl chloride (1.4 mL) was heated at 85° C. for 2 h. The solvent was evaporated and the brown solid was purified by flash column chromatography (silica gel, elution with EtOAc:hexanes, 1:2) to give 0.047 g (50%) of the title compound as a yellow solid. $^1$H NMR (acetone-d$_6$): 7.76 (d, 1H, J=5.5 Hz), 7.16 (d, 1H, J=5.2 Hz), 3.55 (m, 4H), 1.69 (m, 6H).

Compounds of Examples 32-33 were prepared by a procedure similar to that of Example 21 in two steps from 3-chlorothiophene-2-carboxylic acid hydrazide and the corresponding amine-carbonyl chloride.

EXAMPLE 32

5-(3-Chlorothiophen-2-yl)-2-(morpholin-4-yl)-[1,3,4]oxadiazole (a) Morpholine-4-carboxylic acid N-(3-chlorothiophene-2-carbonyl)-hydrazide. $^1$H NMR (CDCl$_3$): 9.16 (br s, 1H), 7.53-7.51 (m, 2H), 7.02-7.00 (m, 1H), 3.73 (t, 4H, J=4.8 Hz), 3.50 (t, 4H, J=4.9 Hz).

(b) 5-(3-Chlorothiophen-2-yl)-2-(morpholin-4-yl)-[1,3,4]oxadiazole. $^1$H NMR (acetone-d$_6$): 7.79 (d, 1H, J=5.5 Hz), 7.17 (d, 1H, J=5.2 Hz), 3.82-3.79 (m, 4H), 3.57-3.54 (m, 4H).

EXAMPLE 33

5-(3-Chlorothiophen-2-yl)-2-(4-methylpiperazin-1-yl)-[1,3,4]oxadiazole (a) 4-Methyl-piperazine-1-carboxylic acid N-(3-chlorothiophene-2-carbonyl)-hydrazide. $^1$H NMR (CDCl$_3$): 9.25 (br s, 1H), 8.00 (br s, 1H), 7.51 (dd, 1H, J=5.4 and 0.7 Hz), 7.00 (dd, 1H, J=5.4 and 0.7 Hz), 3.53 (t, 4H, J=5.1 Hz), 2.43 (t, 4H, J=5.1 Hz), 2.31 (s, 3H).

(b) 5-(3-Chlorothiophen-2-yl)-2-(4-methylpiperazin-1-yl)-[1,3,4]oxadiazole. $^1$H NMR (acetone-d$_6$): 7.74 (d, 1H, J=5.5 Hz), 7.15 (d, 1H, J=5.2 Hz), 3.89-3.84 (m, 4H), 3.44-3.40 (m, 4H), 2.94 (s, 3H).

EXAMPLE 34

4-[5-(3-Bromofuran-2-yl)-[1,2,4]oxadiazol-3-yl]-piperazine-1-carboxylic acid benzyl ester The title compound was prepared in a manner similar to Example 18b. From 4-(N-hydroxycarbaminoyl)-piperazine-1-carboxylic acid benzyl ester (0.100 g, 0.360 mmol), 3-bromofuran-2-carbonyl chloride (0.075 g, 0.360 mmol) and pyridine (0.9 mL) was obtained 0.040 g (26%) of the title compound as a white solid. $^1$H NMR (CDCl$_3$): 7.59 (d, 1H, J=2.0 Hz), 7.38-7.37 (m, 5H), 6.69 (d, 1H, J=1.9 Hz), 5.17 (s, 2H), 3.65-3.62 (m, 4H), 3.54 (m, 4H).

EXAMPLE 35

4-[5-(3-Bromofuran-2-yl)-[1,2,4]oxadiazol-3-yl]-piperazine-1-carboxylic acid tert-butyl ester The title compound was prepared in a manner similar to Example 18b. From 4-(N-hydroxycarbamimidoyl)-piperazine-1-carboxylic acid t-butyl ester (0.470 g, 1.92 mmol), 3-bromofuran-2-carbonyl chloride (0.400 g, 1.92 mmol) and pyridine (4.8 mL) was obtained 0.447 g (58%) of the title compound as a white solid. $^1$H NMR (CDCl$_3$): 7.59 (d, 1H, J=1.9 Hz), 6.68 (d, 1H, J=1.5 Hz), 3.53 (m, 8H), 1.49 (s, 9H).

EXAMPLE 36

5-(3-Chlorothiophen-2-yl)-2-(piperazin-1-yl)-[1,3,4]oxadiazole trifluoroacetic acid salt To a flame-dried reaction flask charged with a magnetic stir bar, was added 4-[5-(3-chlorothiophene-2-yl)-[1,2,4]oxasiazol-3-yl]-piperazine-1-carboxylic acid tert-butyl ester (0.200 g, 0.540 mmol) and TFA (3.33 mL, 43.2 mmol). The yellow solution was stirred at room temperature for 30 min and the solvent was evaporated to give a yellow residue. Dilution with diethyl ether resulted in the formation of a yellow precipitate that was filtered and collected to give 0.171 g (82%) of the title compound as a yellow solid. $^1$H NMR (DMSO-d$_6$): 8.85 (br s, 2H), 8.13 (dd, 1H, J=5.2 and 0.6 Hz), 7.38 (dd, 1H, J=5.2 and 0.6 Hz), 3.62 (t, 4H, J=5.2 Hz), 3.24 (t, 4H, J=5.2 Hz).

EXAMPLE 37

5-(3-Bromofuran-2-yl)-2-(piperazin-1-yl)-[1,3,4]oxadiazole trifluoroacetic acid salt The title compound was prepared in a manner similar to Example 36. From 4-[5-(3-bromofuran-2-yl)-[1,2,4]oxadiazol-3-yl]-piperazine-1-carboxylic acid tert-butyl ester (0.398 g, 1.00 mmol) and TFA (6.20 mL, 80.1 mmol) was obtained 0.260 g (63%) of the titled compound as a white solid. $^1$H NMR (DMSO-d$_6$): 8.91 (br s, 2H), 8.18 (d, 1H, J=1.9 Hz), 7.11 (d, 1H, J=1.9 Hz), 3.63 (t, 4H, J=5.1 Hz), 3.25 (t, 4H, J=5.1 Hz).

EXAMPLE 38

5-(3-Chlorothiophen-2-yl)-3-(4-aminopiperidin-1-yl)-[1,2,4]oxadiazole trifluoroacetic acid salt The title compound was prepared in a manner similar to Example 36. From {1-[5-(3-chlorothiophen-2-yl)-[1,2,4]oxadiazol-3-yl]-piperidin-4-yl}-carbamic acid tert butyl ester (0.050 g, 0.13 mmol) and TFA (0.80 mL, 10 mmol) was obtained 0.030 g (58%) of the title compound as a white solid. $^1$H NMR (DMSO-d$_6$): 8.12 (dd, 1H, J=5.2 and 0.8 Hz), 7.88 (br s, 3H), 7.37 (dd, 1H, J=5.2 and 0.8 Hz), 3.93 (m, 2H, J=12.9 Hz), 3.05 (m, 2H, J=11.5 Hz), 1.96 (m, 2H, J=11.0 Hz), 1.55 (m, 2H, J=12.2 and 4.3 Hz), 1.09 (t, 3H, J=7.0 Hz).

Compounds of Examples 39-48 were prepared by a procedure similar to that of Example 21 in two steps starting from the corresponding arylcarbonitrile and hydroxylamine.

EXAMPLE 39

5-(3-Chlorothiophen-2-yl)-3-(thiophen-2-yl)-[1,2,4]oxadiazole (a) N-Hydroxy-thiophene-2-carboxamidine. $^1$H NMR (DMSO-d$_6$): 9.60 (s, 1H), 7.46 (dd, 1H, J=3.6 and 1.1 Hz), 7.42 (dd, 1H, J=5.2 and 1.1 Hz), 7.04 (dd, 1H, J=5.0 and 3.6 Hz), 5.91 (s, 2H).

(b) 5-(3-Chlorothiophen-2-yl)-3-(thiophen-2-yl)-[1,2,4]oxadiazole. $^1$H NMR (CDCl$_3$): 7.88 (dd, 1H, J=3.6 and 1.2 Hz), 7.61 (d, 1H, J=5.5 Hz), 7.54 (dd, 1H, J=5.0 and 1.2 Hz), 7.18 (dd, 1H, J=5.0 and 3.6 Hz), 7.13 (d, 1H, J=5.2 Hz).

EXAMPLE 40

5-(3-Chlorothiophen-2-yl)-3-(1H-pyrrol-2-yl)-[1,2,4]oxadiazole (a) N-Hydroxy-1H-pyrrole-2-carboxamidine. $^1$H NMR (DMSO-d$_6$): 10.81 (s, 1H), 9.12 (s, 1H), 6.68 (dd, 1H, J=4.1 and 2.5 Hz), 6.43-6.41 (m, 1H), 6.01-5.99 (m, 1H), 5.26 (s, 2H).

(b) 5-(3-Chlorothiophen-2-yl)-3-(1H-pyrrol-2-yl)-[1,2,4]oxadiazole. $^1$H NMR (acetone-d$_6$): 11.08 (br s, 1H), 8.05 (d, 1H, J=5.5 Hz), 7.31 (d, 1H, J=5.2 Hz), 7.11 (m, 1H), 6.91 (m, 1H), 6.32 (m, 1H).

EXAMPLE 41

5-(3-Chlorothiophen-2-yl)-3-(furan-2-yl)-[1,2,4]oxadiazole (a) N-Hydroxy-furan-2-carboxamidine. $^1$H NMR (DMSO-d$_6$): 9.60 (s, 1H), 7.67 (dd, 1H, J=1.7 and 0.8 Hz), 6.75 (dd, 1H, J=3.3 and 0.8 Hz), 6.52 (dd, 1H, J=3.3 and 1.7 Hz), 5.70 (s, 2H).

(b) 5-(3-Chlorothiophen-2-yl)-3-(furan-2-yl)-[1,2,4]oxadiazole. $^1$H NMR (CDCl$_3$): 7.66-7.65 (m, 1H), 7.63-7.61 (m, 1H), 7.24-7.23 (m, 1H), 7.14-7.12 (m, 1H), 6.61-6.59 (m, 1H).

EXAMPLE 42

5-(3-Chlorothiophen-2-yl)-3-(furan-3-yl)-[1,2,4]oxadiazole (a) N-Hydroxy-furan-3-carboxamidine. $^1$H NMR (DMSO-d$_6$): 9.40 (s, 1H), 7.99 (dd, 1H, J=1.5 and 0.7 Hz), 7.64-7.63 (m, 1H), 6.61 (dd, 1H, J=1.9 and 0.8 Hz), 5.68 (br s, 2H).

(b) 5-(3-Chlorothiophen-2-yl)-3-(furan-3-yl)-[1,2,4]oxadiazole. $^1$H NMR (CDCl$_3$): 8.18 (dd, 1H, J=1.4 and 0.8 Hz), 7.60 (d, 1H, J=5.5 Hz), 7.55 (t, 1H, J=1.7 Hz), 7.13 (d, 1H, J=5.2 Hz), 6.95 (dd, 1H, J=1.9 and 0.8 Hz).

EXAMPLE 43

3-(4-Chloro-2-methyl-phenyl)-5-(3-chlorothiophen-2-yl)-[1,2,4]oxadiazole (a) 4-Chloro-N-hydroxy-2-methyl-benzamidine. $^1$H NMR (DMSO-d$_6$): 9.41 (s, 1H), 7.32 (s, 1H), 7.27 (m, 2H), 5.78 (br s, 2H), 2.34 (s, 3 H).

(b) 3-(4-Chloro-2-methyl-phenyl)-5-(3-chlorothiophen-2-yl)-[1,2,4]-oxadiazole. $^1$H NMR (CDCl$_3$): 8.04 (d, 1H, J=8.0 Hz), 7.61 (dd, 1H, J=5.2 and 1.4 Hz), 7.35-7.28 (m, 2H), 7.14 (dd, 1H, J=5.4 and 1.2 Hz), 2.64 (s, 3H).

EXAMPLE 44

5-(3-Chlorothiophen-2-yl)-3-(5-methylfuran-2-yl)-[1,2,4]oxadiazole (a) N-Hydroxy-5-methylfuran-2-carboxamidine. $^1$H NMR (DMSO-d$_6$): 9.46 (s, 1H), 6.62 (t, 1H, J=1.7 Hz), 6.13-6.11 (m, 1H), 5.58 (br s, 2H), 2.27 (s, 3H).

(b) 5-(3-Chlorothiophen-2-yl)-3-(5-methylfuran-2-yl)-[1,2,4]-oxadiazole. $^1$H NMR (CDCl$_3$): 7.60 (d, 1H, J=5.2 Hz), 7.12 (d, 1H, J 5.2 Hz), 7.12 (m, 1H), 6.19 (dd, 1H, J=3.3 and 1.1 Hz), 2.44 (s, 3H).

EXAMPLE 45

5-(3-Chlorothiophen-2-yl)-3-(5-nitrofuran-2-yl)-[1,2,4]oxadiazole (a) N-Hydroxy-5-nitrofuran-2-carboxamidine. $^1$H NMR (DMSO-d$_6$): 10.31 (s, 1H), 7.74 (dd, 1H, J=3.9 and 1.2 Hz), 7.12 (dd, 1H, J=3.8 and 1.3 Hz), 6.06 (br s, 2H).

(b) 5-(3-Chlorothiophen-2-yl)-3-(5-nitrofuran-2-yl)-[1,2,4]oxa-diazole. $^1$H NMR (CDCl$_3$): 7.67 (d, 1H, J=5.5 Hz), 7.45 (d, 1H, J=3.9 Hz), 7.36 (d, 1H, J=3.9 Hz), 7.16 (d, 1H, J=5.2Hz).

EXAMPLE 46

3-(4-Chloro-2-fluoro-phenyl)-5-(3-chlorothiophen-2-yl)-[1,2,4]oxadiazole (a) 4-Chloro-2-fluoro-N-hydroxy-benzamidine. $^1$H NMR (DMSO-d$_6$): 9.73 (s, 1H), 7.55-7.46 (m, 2H), 7.33-7.29 (m, 1H), 5.86 (br s, 2H).

(b) 3-(4-Chloro-2-fluoro-phenyl)-5-(3-chlorothiophen-2-yl)-[1,2,4]-oxadiazole. $^1$H NMR (CDCl$_3$): 8.14-8.09 (m, 1H), 7.62 (d, 1H, J=5.2 Hz), 7.32 (t, 1H, J=2.2 Hz), 7.30-7.28 (m, 1H), 7.14 (d, 1H, J=5.2 Hz).

EXAMPLE 47

5-(3-Chlorothiophen-2-yl)-3-(3-methyl-pyridin-2-yl)-[1,2,4]oxadiazole (a) N-Hydroxy-3-methyl-pyridine-2-carboxamidine. $^1$H NMR (DMSO-d$_6$): 9.84 (d, 1H, J=1.4 Hz), 8.43 (d, 1H, J=4.7 Hz), 7.67 (d, 1H, J 7.4 Hz), 7.31 (dd, 1H, J=7.7 and 4.7 Hz), 5.79 (br s, 2H), 3.33 (s, 3H).

(b) 5-(3-Chlorothiophen-2-yl)-3-(3-methyl-pyridin-2-yl)-[1,2,4]oxadiazole. $^1$H NMR (CDCl$_3$): 8.70 (dd, 1H, J=4.3 and 1.2 Hz), 7.71-7.68 (m, 1H), 7.62 (dd, 1H, J=5.5 and 0.6 Hz), 7.35 (dd, 1H, J=7.8 and 4.5 Hz), 7.13 (dd, 1H, J=5.5 and 0.6 Hz), 2.69 (s, 3H).

EXAMPLE 48

3-(4-Chloro-3-methyl-phenyl)-5-(3-chlorothiophen-2-yl)-[1,2,4]oxadiazole (a) 4-Chloro-N-hydroxy-3-methyl-benzamidine. $^1$H NMR (DMSO-d$_6$): 9.68(s, 1H), 7.65 (d, 1H, J=1.9 Hz), 7.51 (dd, 1H, J=8.2 and 1.9 Hz), 7.40 (d, 1H, J=8.5 Hz), 5.83 (s, 2H), 2.34 (s, 3H).

(b) 3-(4-Chloro-3-methyl-phenyl)-5-(3-chlorothiophen-2-yl)-[1,2,4]-oxadiazole. $^1$H NMR (CDCl$_3$): 8.03 (d, 1H, J=1.6 Hz), 7.93 (m, 1H, J=8.2 and 1.6 Hz), 7.61 (d, 1H, J=5.5 Hz), 7.43 (d, 1H, J=8.2 Hz), 7.13 (d, 1H, J=5.5 Hz), 2.47 (s, 3H).

EXAMPLE 49

5-(3-Bromofuran-2-yl)-3-(4-chloro-2-methyl-phenyl)-[1,2,4]oxadiazole

The title compound was prepared in a manner similar to Example 18b. From 4-chloro-N-hydroxy-2-methyl-benzamidine (0.100 g, 0.542 mmol), 3-bromofuran-2-carbonyl chloride (0.113 g, 0.542 mmol) and pyridine (1.4 mL) was obtained 0.044 g (24%) of the title compound as a brown solid. $^1$H NMR (CDCl$_3$): 8.07 (d, 1H, J=8.2 Hz), 7.67 (dd, 1H, J=1.9 and 0.6 Hz), 7.35-7.30 (m, 2H), 6.75 (dd, 1H, J=1.9 and 0.6 Hz), 2.68 (s, 3H).

EXAMPLE 50

5-(3-Bromofuran-2-yl)-3-(5-chloro-3-methyl-pyridin-2-yl)-[1,2,4]oxadiazole (a) 3-Methyl-5-nitro-pyridine-2-carbonitrile. To a white suspension of 2-cyano-3-methylpyridine (6.08 g, 51.5 mmol), tetrabutylammonium nitrate (21.0 g, 69.0 mmol) in tert-butyl methyl ether (150 mL) at 0° C. was slowly added trifluoroacetic anhydride (9.6 mmol, 69.0 mmol). The white suspension was stirred at 0° C. for 2 h and then equilibrated to room temperature and stirred overnight. The resulting yellow solution was poured into 3M NaOH (300 mL), extracted with CH$_2$Cl$_2$ (300 mL), dried over Na$_2$SO$_4$, and then the solvent was removed by evaporation. The residue was purified by flash column chromatography (silica gel, elution with EtOAc:hexanes, 1:3.5), to give 1.65 g (19%) of the title compound as a white solid. $^1$H NMR (CDCl$_3$): 9.33 (d, 1H, J=2.4 Hz), 8.50 (d, 1H, J=2.4 Hz), 2.74 (s, 3H).

(b) 5-Amino-3-methyl-pyridine-2-carbonitrile. To a hydrogenation flask was added 3-methyl-5-nitro-pyridine-2-carbonitrile (1.65 g, 10.1 mmol), EtOH (37 mL), EtOAc (125 mL) and 5% Pd/C (1.10 g, 0.67% by weight). The resulting black suspension was shaken under $H_2(g)$ at a pressure of 45 psi for 3.5 h. The black suspension was then filtered through a sintered glass funnel containing celite (2 in w×1.5 in h), washing with additional EtOAc (250 mL). The solvent was removed by rotary evaporation to give 1.34 g (100%) of the title compound as a brown solid. 1H NMR (acetone-$d_6$): 7.94 (d, 1H, J=2.5 Hz), 6.94-6.93 (m, 1H), 5.75 (br s, 2H), 2.35 (s, 3H).

(c) 5-Chloro-3-methyl-pyridine-2-carbonitrile. To a brown emulsion of 5-amino-3-methyl-pyridine-2-carbonitrile (1.35 g, 10.1 mmol), copper (I) chloride (2.11 g, 21.3 mmol) and 12 N HCl (3.6 mL) at 0° C. was added slowly a clear solution of sodium nitrite (0.770 g, 11.1 mmol) in water (3.3 mL). The resulting green suspension was stirred at 0° C. for an additional 10 min and then equilibrated to room temperature. The green suspension was then extracted with diethyl ether (4×200 mL), dried over $Na_2SO_4$, and the solvent was removed by evaporation. The residue was purified by flash column chromatography (silica gel, elution with EtOAc:hexanes, 1:5), to give 0.913 g (59%) of the title compound as a white solid. $^1$H NMR (CDCl$_3$): 8.50 (d, 1H, J=2.2 Hz), 7.68 (d, 1H, J=2.2 Hz), 2.57 (s, 3H).

(d) 5-Chloro-N-hydroxy-3-methyl-pyridine-2-carboxamidine. The title compound was prepared in a manner similar to Example 18a. From 5-chloro-3-methyl-pyridine-2-carbonitrile (0.913 g, 5.98 mmol), THF (42 mL) and hydroxylamine (0.74 mL, 12 mmol, 50% wt/water) was obtained 1.07 g (96%) of the title compound as a white solid. $^1$H NMR (DMSO-$d_6$): 9.95 (s, 1H), 8.48-8.47 (m, 1H), 7.88-7.87 (m, 1H), 5.81 (br s, 2H), 2.49 (s, 3H).

(e) 5-(3-Bromofuran-2-yl)-3-(5-chloro-3-methyl-pyridin-2-yl)-[1,2,4]-oxadiazole. The title compound was prepared in a manner similar to Example 18b. From 5-chloro-N-hydroxy-3-methyl-pyridine-2-carboxamidine (1.05 g, 5.65 mmol), 3-bromofuran-2-carbonyl chloride (0.800 g, 6.65 mmol) and pyridine (18.8 mL) was obtained 0.287 g (14%) of the title compound as a white solid. $^1$H NMR (CDCl$_3$): 8.63 (d, 1H, J=2.2 Hz), 7.70 (d, 1H, J=2.2 Hz), 7.67 (dd, 1H, J=1.9 and 1.1 Hz), 6.75 (dd, 1H, J=1.9 and 1.1 Hz), 2.69 (s, 3H).

EXAMPLE 51

{2-Chloro-5-[5-(3-chlorothiophene-2-yl)-[1,2,4]oxadiazol-3-yl]-phenylamino}-acetic acid ethyl ester To a 10 mL microwave reaction flask reaction charged with a magnetic stir bar, was added 2-chloro-5-[5-(3-chlorothiophene-2-yl)-[1,2,4]oxadiazol-3-yl]-phenylamine (0.100 g, 0.320 mmol), anhydrous ethanol (1.3 mL), bromo ethylacetate (0.241 g, 1.44 mmol) and triethylamine (67 μL, 0.48 mmol). The suspension was reacted at 120° C., for 15 min in a microwave set at 70 watts. The resulting yellow suspension was diluted with ethyl acetate (50 mL) and the organic layer was then washed with $H_2O$ (2×15 mL), brine (10 mL), dried over MgSO$_4$, and the solvent was removed by evaporation. The white solid was then purified by flash column chromatography (silica gel, elution with EtOAc: hexanes, 1:5) to yield 0.119 g (94%) of the title compound as a white solid. $^1$H NMR (CDCl$_3$): 7.59 (dd, 1H, J=5.2 and 1.4 Hz), 7.47 (dd, 1H, J=8.3 and 1.7 Hz), 7.38 (dd, 1H, J=8.3 and 1.1 Hz), 7.27 (d, 1H, J=1.7 Hz), 7.10 (dd, 1H, J=5.2 and 1.4 Hz), 5.11 (t, 1H, J=5.0 Hz), 4.29 (q, 2H, J=7.1 Hz), 4.05 (d, 2H, J=5.2 Hz), 1.33 (t, 3H, J=7.1 Hz).

Compounds of Examples 52-53 were prepared by a procedure similar to Example 51.

EXAMPLE 52

N'-{2-Chloro-5-[5-(3-chlorothiophen-2-yl)-[1,2,4]oxadiazol-3-yl]-phenyl}-N,N-diethyl-ethane-1,2-diamine From 2-chloro-5-[5-(3-chlorothiophen-2-yl)-[1,2,4]oxadiazol-3-yl]-phenylamine (0.100 g, 0.320 mmol), anhydrous EtOH (1.3 mL), 2-bromo-N,N-diethylethylamine•HBr (0.334 g, 1.28 mmol) and Et$_3$N (0.230 mL, 1.60 mmol) was obtained 0.006 g (5%) of the title compound as a white solid. $^1$H NMR (acetone-$d_6$): 8.08 (d, 1H, J=5.5 Hz), 7.48-7.37 (m, 3H), 7.34 (d, 1H, J=5.2 Hz), 2.82-2.80 (m, 4H), 2.62-2.58 (m, 4H), 1.07 (t, 6H, J=7.0 Hz).

EXAMPLE 53

{2-Chloro-5-[5-(3-chlorothiophen-2-yl)-[1,2,4]oxadiazol-3-yl]-phenyl}-(2-morpholin-4-yl-ethyl)-amine From 2-chloro-5-[5-(3-chlorothiophen-2-yl)-[1,2,4]oxadiazol-3-yl]-phenylamine (0.100 g, 0.320 mmol), anhydrous EtOH (1.3 mL), 4-(2-chloroethyl)morpholine•HCl (0.238 g, 1.28 mmol), Et$_3$N (0.360 mL, 2.56 mmol) and sodium iodide (0.384 g, 2.56 mmol) was obtained 0.083 g (61%) of the title compound as a white solid. $^1$H NMR (acetone-$d_6$): 8.09 (d, 1H, J=5.5 Hz), 7.48-7.38 (m, 3H), 7.34 (d, 1H, J=5.2 Hz), 3.67 (t, 4H, J=4.7 Hz), 2.84 (d, 2H, J=9.9 Hz), 2.74 (t, 2H, J=6.0 Hz), 2.54-2.52 (m, 4H).

EXAMPLE 54

({2-Chloro-5-[5-(3-chlorothiophen-2-yl)-[1,2,4]oxadiazol-3-yl]-phenyl}-methylamino)-acetic acid ethyl ester To a yellow mixture of (2-chloro-5-[5-(3-chlorothiophene-2-yl)-[1,2,4]oxadiazol-3-yl]-phenylamino)-acetic acid ethyl ester (0.360 g, 0.903 mmol), paraformaldehyde (0.271 g, 9.03 mmol) and glacial acetic acid (4.5 mL) was added sodium cyanoborohydride (0.284 g, 4.51 mmol) in small portions over 5 min. The yellow mixture became a white suspension and was stirred overnight at room temperature. The white suspension was added to a 25% NaOH$_{(aq)}$ solution at 0° C. The aqueous layer was extracted with dichloromethane (50 mL), washed with brine (15 mL), dried over MgSO$_4$, filtered and concentrated in vacuo. The clear oil was purified by flash column chromatography (silica gel, elution with EtOAc:hexanes, 1:5) to yield 0.362 g (96%) of the title compound as a white solid. $^1$H NMR (CDCl$_3$): 7.94 (d, 1H, J=1.7 Hz), 7.73 (td, 1H, J=8.2, 1.9 and 1.7 Hz), 7.61 (dd, 1H, J=5.5, 5.2, 1.6 and 1.4 Hz), 7.45 (dd, 1H, J=8.5 and 1.4 Hz), 7.13 (dd, 1H, J=5.5, 5.2, 1.6 and 1.4 Hz), 4.18 (q, 2H, J=7.1 Hz), 4.04 (s, 2H), 3.07 (s, 3H), 1.26 (t, 3H, J=7.1 Hz).

EXAMPLE 55

({2-Chloro-5-[5-(3-chlorothiophene-2-yl)-[1,2,4]oxadiazol-3-yl]-phenyl}-methylamino)-acetic acid To a white suspension of ({2-chloro-5-[5-(3-chlorothiophene-2-yl)-[1,2,4]oxadiazol-3-yl]-phenyl}-methylamino)-acetic acid ethyl ester (0.362 g, 0.880 mmol) in an EtOH:H$_2$O solution (4:1, 13.4 mL) was added 1M NaOH (0.033 mL, 0.84 mmol). Additional aliquots of 1M NaOH (1.98 mL, 50.34 mmol), ethanol (8 mL) and THF (10 mL)

was added and the mixture was stirred for 2 days until the reaction was complete by TLC. The reaction suspension was neutralized by the addition of 1M HCl and concentrated to a white solid. The white solid was filtered and washed with $H_2O$ and ether to yield 0.142 g (44%) of the title compound as a yellow solid. $^1$H NMR (DMSO-$d_6$): 8.19 (dd, 1H, J=5.2 and 0.8 Hz), 7.79 (s, 1H), 7.52 (dd, 2H, J=8.2 and 6.3 Hz), 7.41 (dd, 1H, J=5.5 Hz), 3.77 (s, 2H), 2.97 (s, 3H).

EXAMPLE 56

({2-Chloro-5-[5-(3-chlorothiophene-2-yl)-[1,2,4] oxadiazol-3-yl]-phenyl}-methylamino)-acetic acid N-hydroxysuccinimidyl ester To a white suspension of ({2-chloro-5-[5-(3-chlorothiophene-2-yl)-[1,2,4]oxadiazol-3-yl]-phenyl}-methylamino)-acetic acid (0.090 g, 0.23 mmol) in anhydrous dichloromethane (2.3 mL) was added N-hydroxysuccinimide (0.027 g, 0.23 mmol) and DCC (0.048 g, 0.23 mmol) and it was stirred for 4 h. To the mixture was added anhydrous DMF (1.4 mL) and the white suspension was stirred for 1 h, filtered through a sintered glass funnel and concentrated in vacuo. The white solid was purified by flash column chromatography (silica gel, elution with EtOAc:hexanes, 1:1) to yield 0.011 g (10%) of the title compound as a white solid. $^1$H NMR (CDCl$_3$): 7.97 (d, 1H, J=2.1 Hz), 7.79-7.76 (m, 1H, J=8.1, 2.4, 0.9 and 0.6 Hz), 7.61 (dd, 1H, J=5.1 and 0.9 Hz), 7.49 (d, 1H, J=8.1 Hz), 7.13 (dd, 1H, J=5.4 and 0.6 Hz), 4.38 (s, 2H), 3.12 (s, 3H), 2.83 (s, 4H).

EXAMPLE 57

5-(3-Bromofuran-2-yl)-3-(3-methyl-pyridin-2-yl)-[1,2,4]oxadiazole

The title compound was prepared in a manner similar to Example 18b. From N-hydroxy-3-methyl-pyridine-2-carboximidine (0.100 g, 0.661 mmol), 3-bromofuran-2-carbonyl chloride (0.138 g, 0.661 mmol) and pyridine (1.7 mL) was obtained 0.098 g (48%) of the title compound as a brown solid. $^1$H NMR (CDCl$_3$): 8.68 (dd, 1H, J=4.7 and 0.6 Hz), 7.71-7.68 (m, 1H), 7.66 (dd, 1H, J=1.9 and 1.1 Hz), 7.36 (d, 1H, J=8.0 and 4.7 Hz), 6.75 (dd, 1H, J=1.9 and 1.1 Hz), 2.68 (s, 3H).

EXAMPLE 58

4-({2-Chloro-5-[5-(3-chlorothiophen-2-yl)-[1,2,4] oxadiazol-3-yl]-phenyl}-methyl-amino)-butyric acid methyl ester (a) 4-Oxo-butyric acid methyl ester. A solution of 4,4-dimethoxy-butyric acid methyl ester (5.00 g, 30.8 mmol), ether (25.0 mL) and 1.2 N HCl (12.0 mL) was stirred at room temperature for 1 h. The reaction was diluted with water (50 mL), extracted with dichloromethane (3×60 mL), dried over Na$_2$SO$_4$ and the solvent was removed by rotary evaporation to give 4.00 g (99%) of the title compound as an oil that was carried forward to the next reaction.

(b) 4-(2-Chloro-5-cyano-phenylamino)-butyric acid methyl ester. To a stirring solution of 3-amino-4-chlorobenzonitrile (1.19 g, 7.83 mmol), glacial acetic acid (1.8 mL, 31 mmol), 4-oxo-butyric acid methyl ester (4.00 g, 31 mmol) and dichloroethane (150 mL) was added sodium triacetoxyborohydride (6.74 g, 31.8 mmol) and the reaction mixture was stirred at room temperature for 15 h. The solvent was removed by rotary evaporation and the residue was diluted with EtOAc (100 mL) and water (50 mL). Saturated NaHCO$_3$ was added until the aqueous layer was neutralized and then the organic layer was collected, dried over Na$_2$SO$_4$, and the solvent was removed by rotary evaporation. The residue was purified by flash column chromatography (silica gel, elution with EtOAc:hexanes, 1:3.5), to give 2.21 g (>100%) of the title compound as a mixture. $^1$H NMR (CDCl$_3$): 7.32 (d, 1H, J=8.0 Hz), 6.90 (dd, 1H, J=8.0 and 1.9 Hz), 4.64 (br s, 1H), 3.71 (s, 3H), 3.25 (q, 2H, J=7.0 Hz), 2.47 (t, 2H, J=7.0 Hz), 2.04 (q, 2H, J=7.0 Hz).

(c) 4-[(2-Chloro-5-cyano-phenyl)-methyl-amino]-butyric acid methyl ester. To a solution of 4-(2-chloro-5-cyano-phenylamino)-butyric acid methyl ester (2.21 g, 8.74 mmol), paraformaldehyde (2.34 g, 78.1 mmol) and glacial acetic acid (80.0 mL) was added sodium cyanoborohydride (2.70 g, 43.0 mmol) and the resulting solution was stirred for 17 h. The solution was diluted with EtOAc (700 mL), washed with saturated NaHCO$_3$ (1200 mL), the organic layer was filtered, dried over Na$_2$SO$_4$, and the solvent was removed by rotary evaporation. The residue was purified by flash column chromatography (silica gel, elution with EtOAc:hexanes, 1:5), to give 1.82 g (87% over the last two steps) of the title compound as a colorless oil. $^1$H NMR (CDCl$_3$): 7.43 (d, 1H, J=8.2 Hz), 7.29 (d, 1H, J=1.6 Hz), 7.21 (dd, 1H, J=8.2 and 1.9 Hz), 3.68 (s, 3H), 3.08 (t, 2H, J=7.4 Hz), 2.80 (s, 3H), 2.39 (t, 2H, J=7.3 Hz), 1.98-1.88 (m, 2H, J=7.4 Hz).

(d) 4-{[2-Chloro-5-(N-hydroxycarbamimidoyl)-phenyl]-methyl-amino}-butyric acid methyl ester. The title compound was prepared in a manner similar to Example 18a. From 4-[(2-chloro-5-cyano-phenyl)-methyl-amino]-butyric acid methyl ester (1.81 g, 6.79 mmol) and hydroxylamine (3×0.420 mL, 20.6 mmol, 50% wt/water) was obtained 1.66 g (81%) of the title compound as a colorless oil. $^1$H NMR (DMSO-$d_6$): 9.69 (s, 1H), 7.46 (d, 1H, J=1.7 Hz), 7.38 (d, 1H, J=8.2 Hz), 7.30 (dd, 1H, J=8.2 and 1.9 Hz), 3.57 (s, 3H), 2.99 (t, 2H, J=7.1 Hz), 2.69 (s, 3H), 2.35 (t, 2H, J=7.3 Hz), 1.81-1.71 (m, 2H).

(e) 4-({2-Chloro-5-[5-(3-chlorothiophen-2-yl)-[1,2,4] oxadiazol-3-yl]-phenyl}-methyl-amino)-butyric acid methyl ester. The title compound was prepared in a manner similar to Example 18b. From 4-{[2-chloro-5-(N-hydroxycarbamimidoyl)-phenyl]-methyl-amino}-butyric acid methyl ester (1.65 g, 5.49 mmol) and 3-chlorothiophene-2-carbonyl chloride (0.995 g, 5.49 mmol) in pyridine (13.0 mL) was obtained 2.16 g (93%) of the title compound as a clear oil. $^1$H NMR (CDCl$_3$): 7.84 (d, 1H, J=1.9 Hz), 7.74 (dd, 1H, J=8.2 and 1.9 Hz), 7.61 (d, 1H, J=5.2 Hz), 7.48 (d, 1H, J=8.2 Hz), 7.13 (d, 1H, J=5.5 Hz), 3.68 (s, 3H), 3.13 (t, 2H, J=7.3 Hz), 2.85 (s, 3H), 2.42 (t, 2H, J=7.4 Hz), 2.00-1.91 (m, 2H).

EXAMPLE 59

4-({2-Chloro-5-[5-(3-chlorothiophen-2-yl)-[1,2,4] oxadiazol-3-yl]-phenyl}-methyl-amino)-butyric acid A solution of LiOH (0.280 g, 6.66 mmol) in H$_2$O (6.0 mL) was added over 1 minute to a solution of 4-({2-chloro-5-[5-(3-chlorothiophen-2-yl)-[1,2,4]oxadiazol-3-yl]-phenyl}-methyl-amino)-butyric acid methyl ester (2.03 g, 4.76 mmol) in THF (55.0 mL) at 0° C. The ice bath was removed and the solution was allowed to equilibrate to room temperature at which point THF (20.0 mL) was added. The resulting suspension was stirred for 21 h and then EtOH (10 mL) was added and the solution was stirred for 10.5 h. The reaction solution was then diluted with 3M NaOH (1.05 mL)

and EtOH (3.0 mL) and stirred for 30 min. The solution was diluted with dichloromethane (100 mL), washed with aqueous NaHCO$_3$ (50 mL), and the solvent was removed by rotary evaporation. The residue was purified by flash column chromatography (silica gel, gradient elution using dichloromethane then EtOAc) to give 1.65 g (84%) of the title compound as a white solid. $^1$H NMR (CDCl$_3$): 7.86 (d, 1H, J=1.9 Hz), 7.76 (dd, 1H, J=8.2 and 1.9 Hz), 7.60 (d, 1H, J=5.2 Hz), 7.49 (d, 1H, J=8.2 Hz), 7.14 (d, 1H, J=5.5 Hz), 3.16 (t, 2H, J=7.0 Hz), 2.85 (s, 3H), 2.48 (t, 3H, J=7.3 Hz), 2.02-1.92 (m, 2H).

EXAMPLE 60

4-({2-Chloro-5-[5-(3-chlorothiophen-2-yl)-[1,2,4]oxadiazol-3-yl]-phenyl}-methyl-amino)-butyric acid N-hydroxysuccinimidyl ester The title compound was prepared by a procedure similar to example 54. From a solution of 4-({2-chloro-5-[5-(3-chlorothiophen-2-yl)-[1,2,4]oxadiazol-3-yl]-phenyl}-methyl-amino)-butyric acid (1.64 g, 3.97 mmol), N-hydroxysuccinimide (0.688 g, 5.98 mmol), DCC (1.21 g, 5.89 mmol) and dichloromethane (60.0 mL) was obtained 1.85 g (91%) of the title compound as a white solid. $^1$H NMR (CDCl$_3$): 7.86 (d, 1H, J=1.9 Hz), 7.76 (dd, 1H, J=8.2 and 1.9 Hz), 7.60 (d, 1H, J=5.2 Hz), 7.49 (d, 1H, J=8.2 Hz), 7.14 (d, 1H, J=5.5 Hz), 3.20 (t, 2H, J=7.1 Hz), 2.86 (s, 3H), 2.84 (br s, 4 H), 2.77 (t, 2H, J=7.3 Hz), 2.12-2.02 (m, 2H).

EXAMPLE 61

4-({2-Chloro-5-[5-(3-chlorothiophen-2-yl)-[1,2,4]oxadiazol-3-yl]-phenyl}-methyl-amino)-1-(4-methyl-piperazin-1-yl)-butan-1-one A solution of 4-({2-chloro-5-[5-(3-chlorothiophen-2-yl)-[1,2,4]oxadiazol-3-yl]-phenyl}-methyl-amino)-butyric acid N-hydroxysuccinimidyl ester (0.128 g, 0.252 mmol), 1-methylpiperazine (0.035 mL, 0.32 mmol) and dichloromethane (5.0 mL) was stirred at room temperature for 25 min and then the solvent was removed by rotary evaporation. The residue was purified by flash column chromatography (silica gel, gradient elution using EtOAc, then EtOAc:MeOH:Et$_3$N, 90:5:5), to give 0.119 g (95%) of the title compound as a colorless oil. $^1$H NMR (CDCl$_3$): 7.85 (d, 1H, J=1.9 Hz), 7.74 (dd, 1H, J=8.2 and 1.9 Hz), 7.62 (d, 1H, J=5.2 Hz), 7.47 (d, 1H, J=8.2 Hz), 7.14 (d, 1H, J=5.2 Hz), 3.63 (t, 2H, J=5.1 Hz), 3.46 (t, 2H, J=5.1 Hz), 3.16 (t, 2H, J=6.9 Hz), 2.85 (s, 3H), 2.43 (t, 2 H, J=7.4 Hz), 2.37-2.35 (m, 4H), 2.29 (s, 3H), 2.01-1.92 (m, 2H).

EXAMPLE 62

N-Butyl-4-({2-Chloro-5-[5-(3-chlorothiophen-2-yl)-[1,2,4]oxadiazol-3-yl]-phenyl}-methyl-amino)-butyramide The title compound was prepared in a manner similar to Example 61. From a solution of 4-({2-chloro-5-[5-(3-chlorothiophen-2-yl)-[1,2,4]oxadiazol-3-yl]-phenyl}-methyl-amino)-butyric acid N-hydroxysuccinimidyl ester (0.0558 g, 0.109 mmol), n-butylamine (0.011 mL, 0.11 mmol) and dichloromethane (6.0 mL) was obtained 0.082 g (75%) of the title compound as an oil. $^1$H NMR (CDCl$_3$): 7.86 (d, 1H, J=1.9 Hz), 7.76 (dd, 1H, J=8.2 and 2.2 Hz), 7.62 (d, 1H, J=5.2 Hz), 7.49 (d, 1H, J=8.2 Hz), 7.14 (d, 1H, J=5.2 Hz), 5.64 (br s, 1H), 3.23-3.19 (m, 2H), 3.14 (t, 2H, J=7.1 Hz), 2.82 (s, 3H), 2.24 (t, 2H, J=7.1 Hz), 2.00-1.92 (m, 2H), 1.43-1.24 (m, 4H), 0.87 (t, 3H, J=7.1 Hz).

EXAMPLE 63

4-({2-Chloro-5-[5-(3-chlorothiophen-2-yl)-[1,2,4]oxadiazol-3-yl]-phenyl}-methyl-amino)-butyric acid octyl ester A solution of 4-({2-chloro-5-[5-(3-chlorothiophen-2-yl)-[1,2,4]oxadiazol-3-yl]-phenyl}-methyl-amino)-butyric acid N-hydroxysuccinimidyl ester (0.0463 g, 0.0909 mmol), n-octanol (2.00 mL, 12.6 mmol) and dichloromethane (2.0 mL) was heated at 175° C. for 40 min, cooled to room temperature, and then the solvent was removed by rotary evaporation. The residue was purified by flash column chromatography (silica gel, elution with EtOAc:hexanes, 1:5), then a second column (elution with EtOAc:hexanes, 1:5), followed by azeotrope evaporation (4× acetone), to give 0.074 g (82%) of the title compound as a colorless oil. $^1$H NMR (CDCl$_3$): 7.84 (d, 1H, J=1.9 Hz), 7.74 (dd, 1H, J=8.2 and 1.9 Hz), 7.61 (dd, 1H, J=5.2 and 0.8 Hz), 7.47 (d, 1H, J=8.2 Hz), 7.14 (dd, 1H, J=5.3 and 0.7 Hz), 4.06 (t, 2H, J=6.7 Hz), 3.13 (t, 2H, J=7.1 Hz), 2.86 (s, 3H), 2.41 (t, 2H, J=7.4 Hz), 2.00-1.91 (m, 2H), 1.62-1.57 (m, 2H), 1.30-1.25 (m, 10 H), 0.90-0.85 (m, 3H).

EXAMPLE 64

{2-Chloro-5-[5-(3-chlorothiophen-2-yl)-[1,2,4]oxadiazol-3-yl]-phenyl}-ethyl-amine To a stirring solution of 2-chloro-5-[5-(3-chlorothiophen-2-yl)-[1,2,4]oxadiazol-3-yl]-phenylamine (0.121 g, 0.386 mmol), (dimethylamino)acetaldehyde diethyl acetal (0.720 mL, 3.94 mmol), glacial acetic acid (24.0 mL) and water (0.100 mL, 5.55 mmol) was added sodium cyanoborohydride (0.140 g, 2.22 mmol). The solution was heated at 60° C. for 5 days and then the solution was stirred at room temperature until a precipitate formed. The suspension was filtered, the filter cake was washed with EtOAc (10 mL) and then the filtrate was concentrated by rotary evaporation. The residue was purified by flash column chromatography (silica gel, elution with EtOAc:hexanes, 1:3.5), gave 0.027 g (20%) of the title compound as a white solid. $^1$H NMR (CDCl$_3$): 7.60 (d, 1H, J=5.2 Hz), 7.44-7.35 (m, 3H), 7.13 (d, 1H, J=5.2 Hz), 4.33 (br s, 1H), 3.37-3.28 (m, 2H), 1.36 (t, 3H, J=7.1 Hz).

EXAMPLE 65

N-{2-Chloro-5-[5-(3-chlorothiophen-2-yl)-[1,2,4]oxadiazol-3-yl]-phenyl}-acetamide The title compound was obtained as a side product during the reaction in Example 64 and obtained in 24% yield as a white solid. $^1$H NMR (CDCl$_3$): 9.14 (br s, 1H), 7.85 (dd, 1H, J=8.5 and 1.9 Hz), 7.64 (br s, 1H), 7.61 (d, 1H, J=5.2 Hz), 7.51 (d, 1H, J=8.2 Hz), 7.12 (d, 1H, J=5.2 Hz), 2.29 (s, 3H).

EXAMPLE 66

3-(3-Bromomethyl-4-chloro-phenyl)-5-(3-chlorothiophen-2-yl)-[1,2,4]oxadiazole

A solution of 3-(4-chloro-3-methyl-phenyl)-5-(3-chlorothiophen-2-yl)-[1,2,4]oxadiazole (1.45 g, 4.66 mmol), NBS (0.923 g, 5.19 mmol), AIBN (0.844 g, 5.14 mmol) and CCl$_4$ (300 mL) was refluxed at 80° C. for 2 h. The solution was cooled to room temperature and additional NBS (0.913 g, 5.13 mmol) and AIBN (0.218 g, 1.33 mmol) was added and the solution was refluxed for 1 h. The solution was cooled to room temperature and stirred for 17 h. TLC indicated that the reaction had not occurred so bromine (0.240 mL, 4.67 mmol) was added and the solution was then brought to reflux. While refluxing, the solution was irradiated with a UV lamp (254 nm, 18.4 watts) for 2 h. The solution was cooled to room temperature, filtered and the solvent was removed by rotary evaporation. The residue was purified by flash column chromatography (silica gel, hexanes:dichloromethane, 8:3), to give 0.808 g (44%) of the title compound as a white solid. $^1$H NMR (CDCl$_3$): 8.24 (d, 1H, J=2.2 Hz), 8.06 (dd, 1H, J=8.5 and 2.2 Hz), 7.63 (d, 1H, J=5.2 Hz), 7.54 (d, 1H, J=8.3 Hz), 7.14 (d, 1H, J=5.2 Hz), 4.66 (s, 2H).

EXAMPLE 67

3-(2-Bromomethyl-4-chloro-phenyl)-5-(3-chlorothiophen-2-yl)-[1,2,4]oxadiazole

The title compound was prepared in a manner similar to Example 66. From a solution of 3-(4-chloro-2-methyl-phenyl)-5-(3-chlorothiophen-2-yl)-[1,2,4]oxadiazole (0.117 g, 0.377 mmol), NBS (0.070 g, 0.40 mmol), AIBN (0.037 g, 0.22 mmol), bromine (0.021 mL, 0.41 mmol) and CCl$_4$ (12.0 mL) was obtained 0.090 g (61%) of the title compound as a white solid. $^1$H NMR (CDCl$_3$): 8.12 (d, 1H, J=8.5 Hz), 7.63 (d, 1H, J=5.2 Hz), 7.57 (d, 1H, J=2.2 Hz), 7.44 (dd, 1H, J=8.5 and 2.2 Hz), 7.15 (d, 1H, J=5.2 Hz), 5.04 (s, 2H).

EXAMPLE 68

3-(4-Chloro-3-pyrrolidin-1-ylmethyl-phenyl)-5-(3-chlorothiophen-2-yl)-[1,2,4]oxadiazole A solution of 3-(3-bromomethyl-4-chloro-phenyl)-5-(3-chlorothiophen-2-yl)-[1,2,4]oxadiazol (0.030 g, 0.077 mmol), pyrrolidine (0.013 mL, 0.16 mmol), Et$_3$N (0.054 mL, 0.39 mmol) and dichloromethane (8.0 mL) was stirred at room temperature for 20 h. The solution was diluted with dichloromethane (30 mL), washed with 10% Na$_2$CO$_3$ (25 mL), dried over Na$_2$SO$_4$, and concentrated. The product was azeotroped with dichloromethane (3×5 mL) and hexanes (2×5 mL) to give 0.028 g (96%) of the title compound as a white solid. $^1$H NMR (CDCl$_3$): 8.27 (d, 1H, J=1.7 Hz), 7.98 (dd, 1H, J=8.2 and 1.9 Hz), 7.61 (d, 1H, J=5.2 Hz), 7.49 (d, 1H, J=8.5 Hz), 7.13 (d, 1H, J=5.2 Hz), 3.85 (s, 2H), 2.67 (br s, 4H), 1.84 (br s, 4H).

Compounds of Examples 69-71 were prepared by a procedure similar to Example 68 from the corresponding bromide and amine.

EXAMPLE 69

3-(4-Chloro-3-dimethylaminomethyl-phenyl)-5-(3-chlorothiophen-2-yl)-[1,2,4]oxadiazole $^1$H NMR (CDCl$_3$): 8.21 (d, 1H, J=1.9 Hz), 7.99 (dd, 1H, J=8.2 and 1.6 Hz), 7.61 (d, 1H, J=5.2 Hz), 7.50 (d, 1H, J=8.2 Hz), 7.13 (d, 1H, J=5.2 Hz), 3.61 (s, 2H), 2.34 (s, 6H).

EXAMPLE 70

3-(4-Chloro-2-pyrrolidin-1-ylmethyl-phenyl)-5-(3-chlorothiophen-2-yl)-[1,2,4]oxadiazole $^1$H NMR (CDCl$_3$): 7.98 (d, 1H, J=8.2 Hz), 7.72 (d, 1H, J=2.0 Hz), 7.61 (d, 1H, J=5.5 Hz), 7.35 (dd, 1H, J=8.4 and 2.0 Hz), 7.14 (d, 1H, J=5.2 Hz), 4.05 (s, 2H), 2.58 (s, 4H), 1.77 (s, 4H).

EXAMPLE 71

3-(4-Chloro-2-dimethylaminomethyl-phenyl)-5-(3-chlorothiophen-2-yl)-[1,2,4]oxadiazole $^1$H NMR (CDCl$_3$): 7.99 (d, 1H, J=8.2 Hz), 7.66 (d, 1H, J=1.9 Hz), 7.61 (d, 1H, J=5.2 Hz), 7.37 (dd, 1H, J=8.5 and 2.2 Hz), 7.13 (d, 1H, J=5.5 Hz), 3.84 (s, 2H), 2.27 (s, 6H).

EXAMPLE 72

Identification of 3-(3-Amino-4-chloro-phenyl)-5-(3-chlorothiophen-2-yl)-[1,2,4]-oxadiazole and Analogs as Caspase Cascade Activators and Inducers of Apoptosis in Solid Tumor Cells Human breast cancer cell lines T-47D and ZR-75-1 were grown according to media component mixtures designated by American Type Culture Collection +10% FCS (Invitrogen Corporation), in a 5% CO$_2$-95% humidity incubator at 37° C. T-47D and ZR-75-1 cells were maintained at a cell density between 50 and 80% confluency at a cell density of 0.1 to 0.6×10$^6$ cells/mL. Cells were harvested at 600×g and resuspended at 0.65×10$^6$ cells/mL into appropriate media+ 10% FCS. An aliquot of 45 µl of cells was added to a well of a 96-well microtiter plate containing 2.5 µl of a 10% DMSO in RPMI-1640 media solution containing 0.16 to 100 µM of 3-(3-amino-4-chloro-phenyl)-5-(3-chlorothiophen-2-yl)-[1,2,4]-oxadiazole or other test compound (0.016 to 10 µM final). An aliquot of 22.5 µL of cells was added to a well of a 384-well microtiter plate containing 2.5 µl of a 10% DMSO in RPMI-1640 media solution without test compound as the control sample. The samples were mixed by agitation and then incubated at 37° C. for 48 h in a 5% CO$_2$-95% humidity incubator. After incubation, the samples were removed from the incubator and 25 µL of a solution containing 14 µM of N-(Ac-DEVD)-N'-ethoxycarbonyl-R110 (SEQ ID No.:1) fluorogenic substrate (Maxim, Inc.; WO99/18856), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model SpectraMax Gemini, Molecular Devices), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - Control\ RFU_{(T=0)} = Net\ RFU_{(T=3h)}$$

The activity of caspase cascade activation was determined by the ratio of the net RFU value for 3-(3-amino-4-chloro-phenyl)-5-(3-chlorothiophen-2-yl)-[1,2,4]-oxadiazole or other test compound to that of control samples. The EC$_{50}$ (nM) was determined by a sigmoidal dose-response calculation (Prism 2.0, GraphPad Software Inc.). The caspase activity (Ratio) and potency (EC$_{50}$) are summarized in Table I:

TABLE I

Caspase Activity and Potency

| | T-47D | |
|---|---|---|
| Example | Ratio | EC$_{50}$ (nM) |
| 1 | 11.9 | 1982 |
| 2 | 15.1 | 1523 |
| 4 | 11.9 | 1854 |
| 7 | 3.4 | 3995 |
| 9 | 9.0 | 3272 |
| 10 | 9.9 | 3749 |
| 13 | 4.4 | 5548 |
| 18 | 2.8 | 5035 |
| 22 | 5.4 | 3321 |
| 43 | 7.9 | 818 |
| 47 | 4.5 | 2440 |
| 49 | 11.9 | 1007 |
| 50 | 5.9 | 797 |
| 57 | 6.4 | 846 |

Thus, 3-(3-amino-4-chloro-phenyl)-5-(3-chlorothiophen-2-yl)-[1,2,4]-oxadiazole (Example 1) and analogs are identified as potent caspase cascade activators and inducers of apoptosis in solid tumor cells.

EXAMPLE 73

Identification of 3-(3-Amino-4-chloro-phenyl)-5-(3-chlorothiophen-2-yl)-[1,2,4]-oxadiazole and Analogs as Antineoplastic Compound that Inhibits Cell Proliferation (GI$_{50}$)

T-47D and SKBr-3 cells were grown and harvested as in Example 72. An aliquot of 90 μL of cells (2.2×10$^4$ cells/mL) was added to a well of a 96-well microtiter plate containing 10 μl of a 10% DMSO in RPMI-1640 media solution containing 1 nM to 100 μM of 3-(3-amino-4-chloro-phenyl)-5-(3-chlorothiophen-2-yl)-[1,2,4]-oxadiazole (0.1 nM to 10 μM final). An aliquot of 90 μL of cells was added to a well of a 96-well microtiter plate containing 10 μL of a 10% DMSO in RPMI-1640 media solution without compound as the control sample for maximal cell proliferation (A$_{Max}$). The samples were mixed by agitation and then incubated at 37° C. for 48 h in a 5% CO$_2$-95% humidity incubator. After incubation, the samples were removed from the incubator and 20 μL of CellTiter 96 AQ$_{UEOUS}$ One Solution Cell Proliferation™ reagent (Promega) was added. The samples were mixed by agitation and incubated at 37° C. for 2-4 h in a 5% CO$_2$-95% humidity incubator. Using an absorbance plate reader (Model 1420 Wallac Instruments), an initial reading (T=0) was made approximately 1-2 min after addition of the solution, employing absorbance at 490 nm. This determines the possible background absorbance of the test compounds. No absorbance for 3-(3-amino-4-chloro-phenyl)-5-(3-chlorothiophen-2-yl)-[1,2,4]-oxadiazole was found at 490 nm. After the 2-4 h incubation, the samples were read for absorbance as above (A$_{Test}$).

Baseline for GI$_{50}$ (dose for 50% inhibition of cell proliferation) of initial cell numbers were determined by adding an aliquot of 90 μL of cells or 90 μL of media, respectively, to wells of a 96-well microtiter plate containing 10 μL of a 10% DMSO in RPMI-1640 media solution. The samples were mixed by agitation and then incubated at 37° C. for 0.5 h in a 5% CO$_2$-95% humidity incubator. After incubation, the samples were removed from the incubator and 20 μL of CellTiter 96 AQ$_{UEOUS}$ One Solution Cell Proliferation™ reagent (Promega) was added. The samples were mixed by agitation and incubated at 37° C. for 2-4 h in a 5% CO$_2$-95% humidity incubator. Absorbance was read as above, (A$_{Start}$) defining absorbance for initial cell number used as baseline in GI$_{50}$ determinations.

Calculation:

GI$_{50}$ (dose for 50% inhibition of cell proliferation) is the concentration where $[(A_{Test}-A_{Start})/(A_{Max}-A_{Start})]=0.5$.

The GI$_{50}$ (nM) are summarized in Table II:

TABLE II

GI$_{50}$ in Cancer Cells

| | GI$_{50}$ (nM) | | | |
|---|---|---|---|---|
| Cell lines | Example 1 | Example 2 | Example 4 | Example 9 |
| T-47D | 894 | 360 | 415 | 514 |
| MX1 | 7000 | 5000 | 210 | 899 |

Thus, 3-(3-amino-4-chloro-phenyl)-5-(3-chlorothiophen-2-yl)-[1,2,4]-oxadiazole (Example 1) and analogs are identified as antineoplastic compound that inhibits cell proliferation.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of treating cancer, wherein the cancer is selected from the group consisting of breast carcinoma, ovarian carcinoma, and lung carcinoma in a human suffering therefrom, comprising administering to a human in need of such treatment an effective amount of a compound having the Formula IV:

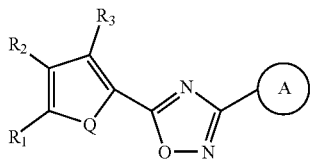

(IV)

or a pharmaceutically acceptable salt or prodrug or tautomers thereof, wherein:

$R_1$-$R_3$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamino, hydroxy, thiol, acyloxy, azido, alkoxy, aryloxy, heteroaryloxy, arylalkoxy, heteroarylalkoxy, haloalkoxy, carboxy, carbonylamido or alkylthiol, each of which is optionally substituted;

Q is S, O or $NR_9$, wherein $R_9$ is hydrogen, optionally substituted alkyl, optionally substituted cycloalkyl or optionally substituted aryl; and Ring A is an optionally substituted heterocycle or carbocycle.

2. The method of claim 1, wherein Q is O or S.
3. The method of claim 1, wherein $R_3$ is not hydrogen.
4. The method of claim 1, wherein ring A is optionally substituted morpholinyl, piperazinyl, piperidinyl or cyclohexyl.
5. The method of claim 1, wherein said compound is selected from the group consisting of:
5-(3-Chlorothiophen-2-yl)-3-(1-piperidinyl)-[1,2,4]-oxadiazole; and
5-(3-Chlorothiophen-2-yl)-3-(4-morpholinyl)-[1,2,4]-oxadiazole,
or a pharmaceutically acceptable salt or prodrug thereof.

6. A method of treating cancer, wherein the cancer is selected from the group consisting of breast carcinoma, ovarian carcinoma, and lung carcinoma in a human suffering therefrom, comprising administering to a human in need of such treatment an effective amount of a compound selected from the group consisting of:
3-(3-Amino-4-chloro-phenyl)-5-(3-chlorothiophen-2-yl)-[1,2,4]-oxadiazole;
5-(3-Chlorothiophen-2-yl)-3-(3-dimethylamino-4-chlorophenyl)-[1,2,4]-oxadiazole;
3-(3-Amino-4-chloro-phenyl)-5-(3-bromofuran-2-yl)-[1,2,4]-oxadiazole;
5-(3-Bromofuran-2-yl)-3-(3-dimethylamino-4-chlorophenyl)-[1,2,4]-oxadiazole;
N-{2-Chloro-5-[5-(3-chlorothiophen-2-yl)-[1,2,4]-oxadiazol-3-yl]-phenyl}-2-(4-methyl-piperazin-1-yl)-acetamide;
N-{2-Chloro-5-[5-(3-chlorothiophen-2-yl)-[1,2,4]-oxadiazol-3-yl]-phenyl}-succinamic acid ethyl ester;
5-(3-Chlorothiophen-2-yl)-3-(4-chloro-3-cyano-phenyl)-[1,2,4]-oxadiazole;
3-(4-Chloro-benzyloxy)-5-(3-chlorothiophen-2-yl)-[1,2,4]-oxadiazole;
5-(3-Chlorothiophen-2-yl)-3-(4-chloro-3-fluoro-phenyl)-[1,2,4]-oxadiazole;
5-(3-Chlorothiophen-2-yl)-3-(4-chloro-3-nitro-phenyl)-[1,2,4]-oxadiazole;
3-(5-Chloro-pyridin-2-yl)-5-(3-methoxy-thiophen-2-yl)-[1,2,4]-oxadiazole;
3-(5-Chloro-pyridin-2-yl)-5-(3-methyl-3H-imidazol-4-yl)-[1,2,4]-oxadiazole;
3-[2-(4-Chloro-phenyl)-vinyl]-5-(3-chlorothiophen-2-yl)-[1,2,4]-oxadiazole;
5-(3-Chloro-1H-pyrrol-2-yl)-3-(5-chloro-pyridin-2-yl)-[1,2,4]-oxadiazole;
3-(4-Chloro-phenyl)-5-(3-chloro-1H-pyrrol-2-yl)-[1,2,4]-oxadiazole;
5-(3-Chloro-1-methyl-1H-pyrrol-2-yl)-3-(4-chloro-phenyl)-[1,2,4]-oxadiazole; and
5-[3-Chloro-1-(2-dimethylaminoethyl)-1H-pyrrol-2-yl]-3-(4-chloro-phenyl)-[1,2,4]-oxadiazole;
5-(3-Chlorothiophen-2-yl)-3-(morpholin-4-yl)-[1,2,4]oxadiazole;
5-(3-Chlorothiophen-2-yl)-3-(pyrrolidin-1-yl)-[1,2,4]oxadiazole;
5-(3-Chlorothiophen-2-yl)-3-(4-methylpiperidin-1-yl)-[1,2,4]oxadiazole;
5-(3-Chlorothiophen-2-yl)-3-(2-methylpiperidin-1-yl)-[1,2,4]oxadiazole;
5-(3-Chlorothiophen-2-yl)-3-(4-trifluoromethylpiperidin-1-yl)-[1,2,4]oxadiazole;
5-(3-Chlorothiophen-2-yl)-3-(4-methylpiperazin-1-yl)-[1,2,4]oxadiazole;
4-[5-(3-Chlorothiophene-2-yl)-[1,2,4]oxadiazol-3-yl]-piperazine-1-carboxylic acid benzyl ester;
4-[5-(3-Chlorothiophene-2-yl)-[1,2,4]oxadiazol-3-yl]-piperazine-1-carboxylic acid tert-butyl ester;
{1-[5-(3-Chlorothiophen-2-yl)-[1,2,4]oxadiazol-3-yl]-piperidin-4-yl}-carbamic acid tert butyl ester;
{1-[5-(3-Chlorothiophen-2-yl)-[1,2,4]oxadiazol-3-yl]-piperidin-4-yl}-acetic acid ethyl ester;
{1-[5-(3-Chlorothiophen-2-yl)-[1,2,4]oxadiazol-3-yl]-piperidin-3-yl}-acetic acid ethyl ester;
5-(3-Chlorothiophen-2-yl)-2-(piperidine-1-yl)-[1,3,4]oxadiazole;
5-(3-Chlorothiophen-2-yl)-2-(morpholin-4-yl)-[1,3,4]oxadiazole;
5-(3-Chlorothiophen-2-yl)-2-(4-methylpiperazin-1-yl)-[1,3,4]oxadiazole;
4-[5-(3-Bromofuran-2-yl)-[1,2,4]oxadiazol-3-yl]-piperazine-1-carboxylic acid benzyl ester;
4-[5-(3-Bromofuran-2-yl)-[1,2,4]oxadiazol-3-yl]-piperazine-1-carboxylic acid tert-butyl ester;
5-(3-Chlorothiophen-2-yl)-2-(piperazin-1-yl)-[1,3,4]oxadiazole trifluoroacetic acid salt;
5-(3-Bromofuran-2-yl)-2-(piperazin-1-yl)-[1,3,4]oxadiazole trifluoroacetic acid salt;
5-(3-Chlorothiophen-2-yl)-3-(4-aminopiperidin-1-yl)-[1,2,4]oxadiazole trifluoroacetic acid salt;
5-(3-Chlorothiophen-2-yl)-3-(thiophen-2-yl)-[1,2,4]oxadiazole;
5-(3-Chlorothiophen-2-yl)-3-(1H-pyrrol-2-yl)-[1,2,4]oxadiazole;
5-(3-Chlorothiophen-2-yl)-3-(furan-2-yl)-[1,2,4]oxadiazole;

5-(3-Chlorothiophen-2-yl)-3-(furan-3-yl)-[1,2,4]oxadiazole;
3-(4-Chloro-2-methyl-phenyl)-5-(3-chlorothiophen-2-yl)-[1,2,4]oxadiazole;
5-(3-Chlorothiophen-2-yl)-3-(5-methylfuran-2-yl)-[1,2,4]oxadiazole;
5-(3-Chlorothiophen-2-yl)-3-(5-nitrofuran-2-yl)-[1,2,4]oxadiazole;
3-(4-Chloro-2-fluoro-phenyl)-5-(3-chlorothiophen-2-yl)-[1,2,4]oxadiazole;
5-(3-Chlorothiophen-2-yl)-3-(3-methyl-pyridin-2-yl)-[1,2,4]oxadiazole;
3-(4-Chloro-3-methyl-phenyl)-5-(3-chlorothiophen-2-yl)-[1,2,4]oxadiazole;
5-(3-Bromofuran-2-yl)-3-(4-chloro-2-methyl-phenyl)-[1,2,4]oxadiazole;
5-(3-Bromofuran-2-yl)-3-(5-chloro-3-methyl-pyridin-2-yl)-[1,2,4]oxadiazole;
{2-Chloro-5-[5-(3-chlorothiophene-2-yl)-[1,2,4]oxadiazol-3-yl]-phenylamino}-acetic acid ethyl ester;
N'-{2-Chloro-5-[5-(3-chlorothiophen-2-yl)-[1,2,4]oxadiazol-3-yl]-phenyl}-N,N-diethyl-ethane-1,2-diamine;
{2-Chloro-5-[5-(3-chlorothiophen-2-yl)-[1,2,4]oxadiazol-3-yl]-phenyl}-(2-morpholin-4-yl-ethyl)-amine;
({2-Chloro-5-[5-(3-chlorothiophene-2-yl)-[1,2,4]oxadiazol-3-yl]-phenyl}-methylamino)-acetic acid ethyl ester;
({2-Chloro-5-[5-(3-chlorothiophene-2-yl)-[1,2,4]oxadiazol-3-yl]-phenyl}-methylamino)-acetic acid;
({2-Chloro-5-[5-(3-chlorothiophene-2-yl)-[1,2,4]oxadiazol-3-yl]-phenyl}-methylamino)-acetic acid N-hydroxysuccinimidyl ester;
5-(3-Bromofuran-2-yl)-3-(3-methyl-pyridin-2-yl)-[1,2,4]oxadiazole;
4-({2-Chloro-5-[5-(3-chlorothiophen-2-yl)-[1,2,4]oxadiazol-3-yl]-phenyl}-methyl-amino)-butyric acid methyl ester;
4-({2-Chloro-5-[5-(3-chlorothiophen-2-yl)-[1,2,4]oxadiazol-3-yl]-phenyl}-methyl-amino)-butyric acid;
4-({2-Chloro-5-[5-(3-chlorothiophen-2-yl)-[1,2,4]oxadiazol-3-yl]-phenyl}-methyl-amino)-butyric acid N-hydroxysuccinimidyl ester;
4-({2-Chloro-5-[5-(3-chlorothiophen-2-yl)-[1,2,4]oxadiazol-3-yl]-phenyl}-methyl-amino)-1-(4-methyl-piperazin-1-yl)-butan-1-one;
N-Butyl-4-({2-Chloro-5-[5-(3-chlorothiophen-2-yl)-[1,2,4]oxadiazol-3-yl]-phenyl}-methyl-amino)-butyramide;
4-({2-Chloro-5-[5-(3-chlorothiophen-2-yl)-[1,2,4]oxadiazol-3-yl]-phenyl}-methyl-amino)-butyric acid octyl ester;
{2-Chloro-5-[5-(3-chlorothiophen-2-yl)-[1,2,4]oxadiazol-3-yl]-phenyl}-ethyl-amine;
N-{2-Chloro-5-[5-(3-chlorothiophen-2-yl)-[1,2,4]oxadiazol-3-yl]-phenyl}-acetamide;
3-(3-Bromomethyl-4-chloro-phenyl)-5-(3-chlorothiophen-2-yl)-[1,2,4]oxadiazole;
3-(2-Bromomethyl-4-chloro-phenyl)-5-(3-chlorothiophen-2-yl)-[1,2,4]oxadiazole;
3-(4-Chloro-3-pyrrolidin-1-ylmethyl-phenyl)-5-(3-chlorothiophen-2-yl)-[1,2,4]oxadiazole;
3-(4-Chloro-3-dimethylaminomethyl-phenyl)-5-(3-chlorothiophen-2-yl)-[1,2,4]oxadiazole;
3-(4-Chloro-2-pyrrolidin-1-ylmethyl-phenyl)-5-(3-chlorothiophen-2-yl)-[1,2,4]oxadiazole; and
3-(4-Chloro-2-dimethylaminomethyl-phenyl)-5-(3-chlorothiophen-2-yl)-[1,2,4]oxadiazole;

or a pharmaceutically acceptable salt or prodrug thereof.

7. The method of claim 1 or 6, wherein said cancer is drug resistant cancer.

8. The method of claim 1 or 6, further comprising administering at least one known cancer chemotherapeutic agent, or a pharmaceutically acceptable salt of said agent.

9. The method according to claim 1 or 6, wherein said compound is administered together with at least one compound selected from the group consisting of busulfan, cisplatin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, arsenic trioxide, gamcitabine, doxazosin, terazosin, tamsulosin, CB-64D, CB-184, haloperidol, lovastatin, simvastatin, pravastatin, fluvastatin, atorvastatin, cerivastatin, amprenavir, abacavir, CGP-73547, CGP-61755, DMP-450, indinavir, nelfinavir, tipranavir, ritonavir, saquinavir, ABT-378, AG 1776, BMS-232,632, bexarotene, tretinoin, 13-cis-retinoic acid, 9-cis-retinoic acid, α-difluoromethylornithine, ILX23-7553, fenretinide, N-4-carboxyphenyl retinamide, lactacystin, MG-132, PS-341, imatinib mesilate ZD1839 (Iressa), SH268, genistein, CEP2563, SU6668, SU11248, EMD121974, R115777, SCH66336, L-778,123, BAL9611, TAN-1813, flavopiridol, UCN-01, roscovitine, olomoucine, celecoxib, valecoxib, rofecoxib and alanosine.

10. The method of claim 1 or 6, further comprising treating said human with radiation-therapy.

11. The method of claim 1 or 6, wherein said compound is administered after surgical treatment of said human for said cancer.

12. The method of claim 1 or 6, wherein said cancer is breast carcinoma.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Asp Glu Val Asp
1
```